(12) United States Patent
Pelletier

(10) Patent No.: US 7,078,913 B1
(45) Date of Patent: Jul. 18, 2006

(54) MULTIPATH RESISTANT MICROWAVE MOISTURE SENSOR

(75) Inventor: Mathew G. Pelletier, Lubbock, TX (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 10/749,484

(22) Filed: Dec. 31, 2003

(51) Int. Cl.
*G01R 27/04* (2006.01)

(52) U.S. Cl. .................. 324/640; 324/76.56; 73/73

(58) Field of Classification Search ............... 324/603, 324/605, 637–644; 73/73
See application file for complete search history.

(56) References Cited

U.S. PATENT DOCUMENTS

| | | | |
|---|---|---|---|
| 3,851,244 A * | 11/1974 | Mounce | 324/640 |
| 4,135,131 A * | 1/1979 | Larsen et al. | 324/639 |
| 4,361,801 A | 11/1982 | Meyer et al. | 324/638 |
| 5,256,978 A | 10/1993 | Rose | 324/601 |
| 5,845,529 A | 12/1998 | Moshe et al. | 73/73 |
| 5,939,888 A * | 8/1999 | Nelson | 324/640 |
| 6,107,809 A | 8/2000 | Moshe et al. | 324/640 |
| 6,111,415 A | 8/2000 | Moshe | 324/640 |
| 6,278,412 B1 | 8/2001 | Kelly et al. | 343/786 |
| 6,466,168 B1 * | 10/2002 | McEwan | 342/465 |
| 6,476,619 B1 | 11/2002 | Moshe et al. | 324/634 |

OTHER PUBLICATIONS

U.S. Appl. No. 60/533,843, filed Feb. 4, 2003, Mathew G. Pelletier.

* cited by examiner

*Primary Examiner*—Vincent Q. Nguyen
(74) *Attorney, Agent, or Firm*—John D. Fado; Randall E. Deck; Lesley Shaw

(57) ABSTRACT

The moisture content of a test material may be determined using a microwave-based process and device which is free from interference by multipath standing waves. Multipath signals may be electronically removed from the measured signal.

25 Claims, 17 Drawing Sheets

Magnitude (dB)

Magnitude (dB)

MULTIPATH RESISTANT MICROWAVE MOISTURE SENSOR

BACKGROUND OF THE INVENTION

1. Field of the Invention

The invention relates to an improved microwave system for measuring the moisture content of cotton bales and other materials.

2. Description of the Prior Art

Modern cotton gins have the purpose of extracting lint (the cotton) from trash and seeds—usually the sticks, leaves and burrs that are entrained with the cotton. These modern gins include many individual machine components that are operated sequentially to form the gin processing line. The components are often specific in the types of trash that they remove. Stick machines, inclined cleaners, and especially lint cleaners process the lint to a purity where it can be baled and delivered to spinning mills. Included in these systems are drying systems as it is imperative that the cotton must be within a range of moisture contents in order for the machinery to work properly.

Unfortunately, the cotton processed by such machines varies widely in moisture content and to date the technology available to measure the moisture content is limited to inaccurate low cost resistance moisture sensors or extremely expensive microwave moisture sensors. Thus, only a very few cotton gins are even attempting to measure the moisture content even though control over the moisture content is critical to the operation of the cotton gin in terms of both productivity as well as for the preservation of the required quality standard for the ultimately produced lint cotton.

This need to produce a better quality product for sale to the cotton textile mills and to reduce labor costs during processing has led to considerable interest in process control for cotton gins. Anthony and Byler (1994) indicate that process control can range from $15,000 to $100,000. Most of the work to date has involved the online measurement of moisture and trash. It is inevitable that the cotton gins in the near future will become fully computerized and automated (Byler and Anthony, 1997). This is due to the fact that optimal control of the gin will produce optimal economic returns for a given ginned bale of cotton. This will be advantageous to the growers, the ginners, and the processing mills as they will receive a consistent product that can be tailored to their desired specifications. In this regard, it is expected that the gins will become fully automated in the near future as suitable low cost technology becomes available. It has already been shown that this automation will utilize some form of moisture measurement system at several key locations scattered throughout the ginning process.

Byler and Anthony (1997) reported on a computer-based cotton color and trash and moisture measurement system that was used to control the drying and cleaning machinery. This system utilizes a resistance sensor. The system can only be made to work when used in conjunction with a sampling system that presents a solid piece of lint (no voids or holes) and at a uniform packing density to remove the effect of varying lint density from the measurement. This system was installed at a gin in Cortland, Ala. in 1994. In 1994, it was reported to be the most complete computerized gin process control system in the world. This process control system utilized two trash and moisture level sensors. The cotton moisture/color/trash sensors were based upon the High-Volume-Instruments (HVI) that are used in the United States Department of Agriculture's Cotton Classing Office. The first sensor was located opposite of a ram located in the back of the feed control. The feed control is located before the gin stand where the lint is removed from the seed cotton. The ram was periodically extended to press cotton against a glass sample imaging and resistance sensing plate. The second color/trash/moisture measurement station was located after the gin stand and before the lint cleaners. A paddle sampler was used to obtain a sample from the duct and press the sample against a sensing window.

Byler (1992) reported that sample compression against a resistance sensing plate was used to increase the sample density in order to produce a more repeatable moisture reading by minimizing the sample density variations. The sample compression was felt to be important enough that several devices were developed to accomplish this and U.S. Pat. No. 5,125,279 Jun. 30, 1992 entitled System for Analyzing Cotton was obtained for a paddle sampler to accomplish the sample extraction compression for the trash, moisture and color measurement, as well as the moisture sensing patent U.S. Pat. No. 5,514,973 which is based upon resistance sensing. It is still in use to date in the Zellweger Uster Intelligin and was reported to be fully functional in two commercial gin's as conducted in a USDA study (Anthony et al., 1995).

Another disadvantage to this technique is the need for pressing the cotton against a resistance sensing plate, as this restricts the possible locations where this technique can be applied in a cotton gin in addition to the very likely possibility of stoppage/blockage of the cotton flow due to system malfunctions.

The final stage in the cotton processing stream is the cotton bale packaging system. Recent innovations has shown that the use of cotton moisture restoration systems both reduce stress on the pale packaging system as well as add additional weight to the bales. As cotton is sold on a wet basis there is a real market incentive for the utilization of these systems. As such, currently there are no resistive sensors that can be accurately used to control these systems as the surface moisture these systems add to the cotton alter the calibration of these sensors in an uncontrolled manner. The only other types of sensors that can be utilized are very expensive microwave bale moisture sensors that are typically utilizing very high frequency microwave technology that is prohibitively expensive to manufacture. Given this fact there are a large number of cotton gins that are using moisture restoration systems without any type of feed back control sensor to maintain the correct moisture in the cotton bales.

Cotton bales are provided an official grade that is based upon samples obtained immediately upon the baling of the cotton. These samples are shipped to a USDA-AMS classing office where both the color and trash content are measured. This grade is then used to set the value of that particular bale of cotton. Unfortunately, when moisture is added to the bale in an excessive amount, this grade has been shown to change as the moisture degrades the cotton. This has led to hundreds of bales being returned back to the gins and has caused a great deal of concern in the industry over the potential damage to the USDA-AMS classing grade. Given this situation it is critical that a low cost moisture measurement system is developed that will determine the moisture content of the cotton bales. This system could then be easily deployed at an affordable price to all gins that are using moisture restoration and will protect and maximize the quality and value of their cotton as well as preserve and protect the reputation of US cotton and USDA-AMS cotton grades.

In the field of non-contact moisture sensing, there exists two main styles of radio frequency sensing systems, near and far field detection. An example of a near field system which is based upon a very low frequency rf field measurement, U.S. Pat. No. 6,275,046. This system utilizes a near-field electric field measurement which to date has demonstrated poor repeatability, low accuracy and severe drift over time problems. Other more relevant instruments of note are of several microwave sensor patents.

U.S. Pat. No. 2,659,860 teaches a method to measure the moisture content of bales of material, by directing a 10 GHz microwave beam through the bale and receiving the beam with another antenna on the far side of the bale from the one which generated the signal. The moisture content of the bale is then determined solely from the attenuation of this signal.

Meyer and Schilz U.S. Pat. No. 4,361,801 teaches a sensing technique that requires measurements of both attenuation and the phase delay of propagation in order to calculate the real and the imaginary components of the complex permittivity measurement in order to measure moisture at 9 GHz which is independent of density. The basis for this measurement is the ratio of the complex permittivities providing, which is a modification of taking the ratio of the attenuation to the propagation delay, as the measure of moisture (either as phase delay or equivalently the time delay). Nelson et al. U.S. Pat. No. 6,147,503 describes another moisture sensor algorithm that provides a moisture sensor that is independent of density over the narrow range of densities provided by loose seed kernel samples versus tightly packed seed kernel samples. They teach a technique that operates at 11.3 and 18 GHz again using both the attenuation and the propagation delay to calculate the complex permittivity of the material to derive an algorithm for the determination of the moisture content of the material. Moshe et al. U.S. Pat. No. 6,476,619 describes a microwave cavity perturbation technique for the sensing of moisture and or density in cotton sliver that has a preferred operating range of 7–9 GHz. In the perturbation technique the system is setup with a resonant peak in the signal amplitude versus frequency plot and utilizes the frequency change in the location of this peak as the measure of permittivity change thereby providing a measure of the permittivity from which the moisture content can be estimated assuming a constant density of material. Moshe et al. U.S. Pat. No. 6,111,415 describes the use of the well known radar technique of Frequency Modulated Time Domain "FMTD" for use as a density sensor which is used to correct an attenuation based moisture sensor. Other patents by Moshe et al. include U.S. Pat. Nos. 5,845,529 and 6,107,809 which utilize a ratio of attenuation to phase delay measurement in a manner very similar to the Meyer and Schilz U.S. Pat. No. 4,361,801. The reoccurring theme between all of these patents is that they all use very high microwave frequencies, typically above 7 GHz, and all of them utilize a measure of the attenuation of the signal after it has been transmitted through the material under test as the primary measure of the moisture content. As such, all of these patents provide very expensive solutions. Additionally it should be noted that the radar cross-section of the typical metal bale ties is very large at these high microwave frequencies and has been shown to cause significant signal interference at these very high frequencies, thereby rendering all of these frequencies unusable for use in moisture measurement of metal tied cotton bales.

In today's modern cotton gins, all of the US cotton gins are housed in metal clad structures. When utilizing microwave and radio frequency based sensors in such buildings, standing waves are setup that cause significant interference with the measurement. The interference affects both the signal strength (attenuation) measurement as well as the propagation phase delay measurement. This interference degrades the accuracy of these systems and in most situations renders the technique unusable and makes it impossible to calibrate the system ahead of time at the factory. Thus, the units are shipped uncalibrated and must be installed with expensive and elaborate field calibration techniques that add significant cost to the system as the manufacturer must pass on this added cost of doing business. Thus, it is a primary goal of this invention to provide a method by which to produce a system that provides a measurement of moisture that is installation independent and is only dependant upon the material's permittivity. In order to accomplish this, the invention as described herein removes from the measurement the multi-path interferences and utilizes a low microwave frequency to avoid interference from spurious emissions from metal-tied cotton bales. It should be noted that as described this system will work equally well with non-metal bale tied cotton bales.

SUMMARY OF THE INVENTION

I have now invented a novel microwave-based process and device for determining the moisture content of a test material free from interference by multipath standing waves. By virtue of this invention, these multipath signals may be electronically removed from the measured signal. The process of the invention includes the steps of:

producing a primary microwave signal with a varying frequency, this signal may be a continuously varying signal or a discrete time varying signal, splitting the primary signal to provide first and second microwave signals, wherein the first signal is transmitted through said material and the second signal provides an internal reference signal, transmitting the first signal through at least a portion of the material, receiving a third signal at a receiver, wherein the third signal includes the first signal after it has passed through the material possibly in combination with multi-path interference signals from the surrounding area that may or may not have passed through the material, mixing the third signal together with the second signal, generating a mixed signal, filtering the mixed signal to remove substantially all of the multi-path interference signals, generating a filtered-mixed signal, measuring the frequency of the filtered-mixed signal and calculating the moisture content of said material, wherein the frequency of the primary signal varies sufficiently rapidly that the frequency of the third signal and the second signal will be different when they arrive at the mixer.

The invention also relates to an apparatus for automatically determining the moisture content of a test material. The apparatus includes a microwave signal generator effective for producing a microwave signal with a continuously varying frequency, microwave signal transmitter and receiver effective to transmit and receive a microwave signal through the material, a microwave mixer, an analog or an analog plus digital microwave signal filter, and a frequency detector. The apparatus also includes a microprocessor effective for calculating the moisture content from the frequency of the filtered-mixed signal.

In accordance with this discovery, it is an object of this invention to provide an improved microwave process and system for measuring the moisture content of cotton bales and other materials.

It is also an object of this invention to provide a process and system for measuring moisture content free from interference by multipath interference signals.

Other objects and advantages of the invention will become readily apparent from the ensuing description.

DETAILED DESCRIPTION OF THE INVENTION

Figure 1A:
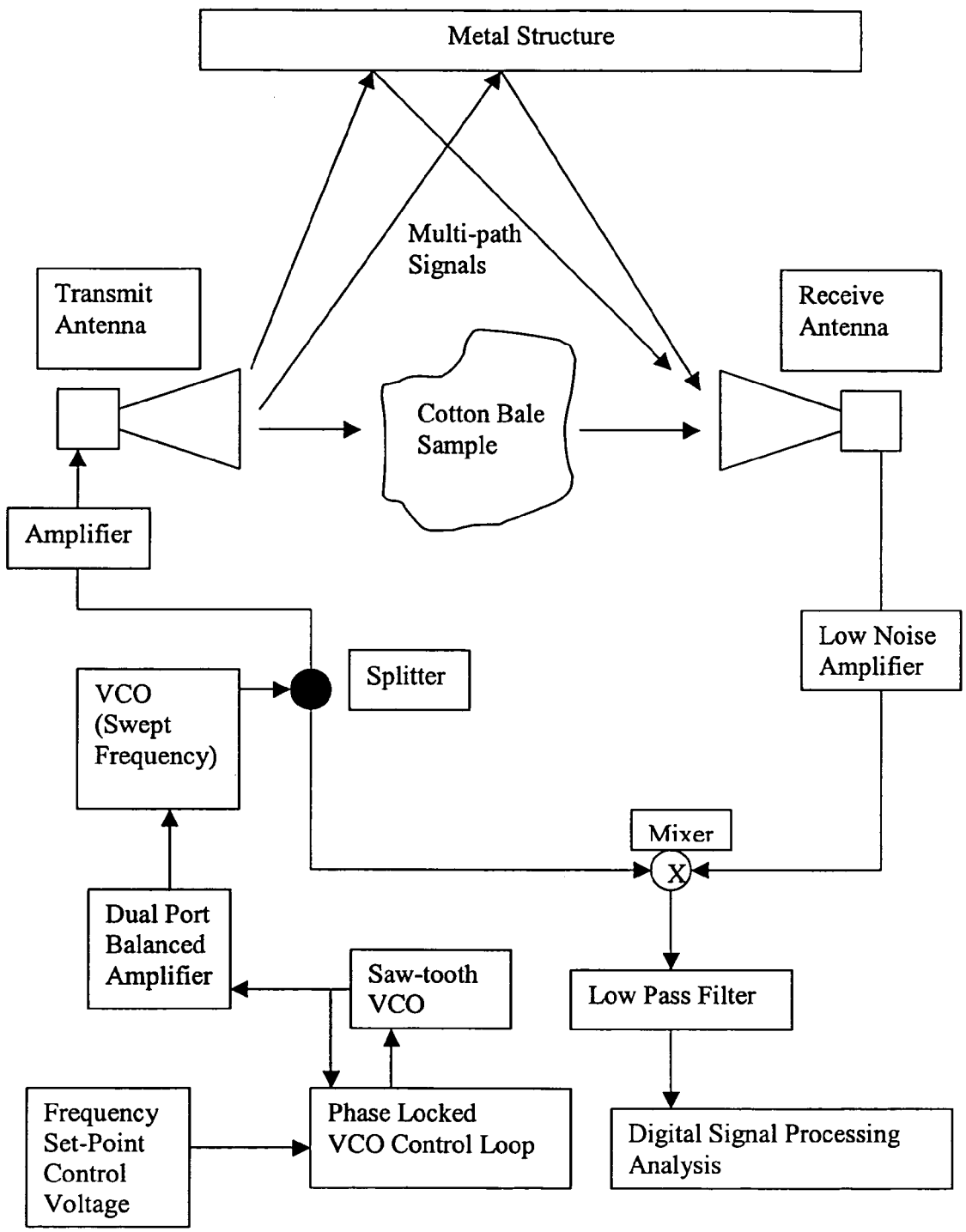
FIG. 1a is a schematic layout of the microwave cotton bale moisture sensor with multi-path interference.

In the transmission of microwave energy, a large portion of the signal being transmitted goes out the side and the back of the transmitting antenna in a direction away from the target of the receiving antenna (Cheng, D. K. 1992. Field and Wave Electromagnetics, $2^{nd}$ Ed., Addison-Wesley Publishing Co. Reading, Mass.)(Balanis, C. A. 1982. Antenna Theory, analysis and design. New York, Harper & Row). In addition to this stray radiation more energy is reflected off the front face of the cotton bale (Pozar, D. M., 1998. Microwave Engineering, $2^{nd}$ Ed., New York: Wiley). Through the use of directional focusing antennas such as microwave dishes and horns, the amount of stray radiation can be reduced, but it will still push a significant amount of energy into the off axis directions. This off axis energy provides the majority of energy for the multi-path interference. In most field applications for use in cotton gins, the units are placed into operation within a metal building. Thus, virtually all radiation that is not directed through the cotton bale is energy that is likely to become available for multi-path interference. This stray energy that is released inside this metal cavity is free to be redirected back to the receiving antenna by any metal reflectors in the vicinity. Thus, the stray radiation bounces around until it is either absorbed by an object or is absorbed at the receiving antenna as multi-path interference. In a cotton gin, there are an ample number of reflectors due to all the machinery as well as the metal walls and roof of the building. This fact gives rise to a large number of multi-path interfering signals. This combination of the multi-path signals with the direct path signal results in the reception of a series of sinusoids of the same frequency but with an altered phase and magnitude at the receiving antenna.

Multi-path interference is a term commonly used in the telecommunications industry for the situation where the direct path received microwave energy is being combined with microwave energy that has been delayed by reflecting off neighboring reflectors (Lee, J. S., L. E. Miller. 1998. CDMA Systems Engineering Handbook. Artech House, Boston, Mass.)(Sremler, F. G., 1992. Introduction to Communication Systems, $3^{rd}$ Ed., Reading, Mass.: Addison-Wesley). As this reflected energy takes a longer path to reach the antenna, it is out of phase and typically of a smaller amplitude than the direct path energy. This energy typically combines out of phase with the direct path energy leading to reduced signal strength due to destructive signal combination. This phenomenon is a well known issue and numerous modulation schemes have been devised to mitigate this effect. Perhaps the best well known technique is the cellular phone industries CDMA or code-division-multiple-access system. This technique is a spread-spectrum phase modulation scheme that relays on spreading the signal over a very wide frequency bandwidth and then using a low frequency pseudo-random-noise (pn) chipping signal that is combined with the desired digital signal. This combined signal is then used to modulate a high-frequency microwave carrier. Upon reception at the receiving antenna, the pn vector is used to demodulate the received carrier. This system works extremely well at removing multi-path interference as it uses the redundancy of the low frequency pn signal to reject the spurious signals impinging upon the receiving antenna that are created by the multi-path signals (Lee and Miller, ibid).

Unfortunately, for microwave moisture sensing, we rely upon the resolution provided by the un-modulated carrier signal with a frequency over 1.5 GHz. As such, the spread spectrum technique cannot be utilized with today's technology as we can't build a digital synthesizer that can operate above 80 MHz. Only at some future time when we can design digital synthesizers that operate at well above 10 GHz can we expect to utilize these techniques in microwave moisture sensing.

A typical model used in the telecommunication industry for multi-path interference utilizes the addition of two or three delayed versions of the direct path signal to form a composite received signal at a reduced magnitude that is typically very much less than 1 (Stremler, ibid). The reduction in magnitude is allowed as it is representative of the real-world phenomenon. In mathematical terms, this signal combination is illustrated in equation 1:

$$S(t) = s(t) + a_0 \cdot s(t+t_1) + a_1 \cdot s(t+t_2) + a_2 \cdot s(t+t_3) \quad (1)$$

where $S(t)$: = the received signal as a function of time (t).

$s(t)$: = the transmitted signal as a function of time (t).

$s(t+t_i)$: = the time delayed version of the transmitted signal or multi-path signal.

$a_{0-3}$: = reduction coefficients where $a \ll 1$.

If a microwave moisture sensing system used a continuous wave signal to transmit microwaves through a cotton bale, multipath interference signals would generate a set of like frequency sinusoids of various amplitudes and phases the sum of which would produce a single sinusoid at the same frequency with an altered amplitude and phase. This would unpredictably alter the direct path signal's amplitude and phase that are the basis for the microwave permittivity measurement.

To overcome this problem, this invention utilizes a frequency modulated signal that can be examined after heterodyning the signal down to a lower and more manageable frequency.

The radio heterodyning signal mixing equation, where two signals are combined together in a mixer to form a new signal that is at both a sum and difference frequency (Stremler, ibid), is illustrated. Mathematically this is equivalent to a multiplication of the two signals together as shown in equation (2):

$$Y(t) = 2\sin(\omega_1 t)\sin(\omega_2 t) \quad (2)$$
$$= \cos(\omega_1 t - \omega_2 t) - \cos(\omega_1 t + \omega_2 t)$$
$$= \cos(\{\omega_1 - \omega_2\}t) - \cos(\{\omega_1 + \omega_2\}t)$$

Expanding equation 2 to include the phase terms leads to equation 3 and 4:

$$Z(t) = 2\sin(\omega_1 t + \varphi_1)\sin(\omega_2 t + \varphi_2) \quad (3)$$
$$= \cos(\omega_1 t + \varphi_1 - \omega_2 t - \varphi_2) - \cos(\omega_1 t + \varphi_1 + \omega_2 t + \varphi_2)$$

and letting $\phi_3 = \phi_1 - \phi_2$ and $\phi_4 = \phi_1 + \phi_2$ then $$Z(t) = \cos(\{\omega_1 - \omega_2\}t + \omega_3) - \cos(\{\omega_1 + \omega_2\}t + \omega_4) \quad (4)$$

In the use of a microwave permittivity measurement system, it is critical that the phase and the magnitude of the signal are preserved. To examine the potential for use of a mixer in the system, let the first signal be the reference signal and in doing so let it's phase be equal to zero and the amplitude equal to unity. Signal two will be the received direct path signal with an altered phase and magnitude. Given this assumption, the applied form of equation 4 is shown in equation 5:

$$Z(t) = \sin(\omega_1 t) A \cdot \sin(\omega_2 t + \varphi_2) \quad (5)$$
$$= 0.5 \cdot A[\cos(\{\omega_1 - \omega_2\}t - \varphi_2) - \cos(\{\omega_1 + \omega_2\}t + \varphi_2)]$$

The final operation is to pass the signal through a low pass filter operation in order to remove the upper band portion of the signal (equation 6):

$$Z(t) * Lp(t) = 0.5 \cdot A \cos(\{\omega_1 - \omega_2\}t - \omega_2) \quad (6)$$

Where $Z(t)*Lp(t)$: = convolution of signal $Z(t)$ with the low pass linear filter $Lp(t)$.

Note that both the amplitude as well as the phase information contained in cotton altered signal number two are preserved in both the upper-side band ($\omega_1 + \omega_2$) as well as the lower side band ($\omega_1 - \omega_2$) of the carrier modulated signal. Thus, the signal can be translated from one frequency to another without loss of amplitude and phase information as long as the signal is mixed against a known reference frequency. For ease of processing the system then removes one of these side bands through either analog or digital filtering.

This provides the basis for this invention with the primary goal to shut out any signal that is delayed beyond the expected direct path delay. To achieve this goal, the invention varies the reference transmit frequency so that it is continuously varying or discretely varying, such that the frequency varies sufficiently rapidly that the frequencies of the signal transmitted through the material and the reference signal will be different when they are received at the receiver. This reference frequency is then combined with the received signal in a mixer to produce the sum and difference frequencies. The sum frequency is removed through filtering and the remaining difference frequency is due to the propagation delay of the direct path signal times the rate of the frequency variation. Thus, by providing a known rate of frequency variation, this difference frequency provides a direct measure of the propagation delay (otherwise known as the phase velocity, phase delay or time delay) due to the transmission through a dielectric material.

This technique results in the direct path having a small difference or delta frequency and a much larger delta frequency for the multi-path signals as they will take longer to arrive at the receive antenna than the direct path signal. This frequency difference between the direct path and the multi-path components allows for direct removal of the multi-path components by means of a band-pass filter centered around the expected delays of the direct path signal.

An additional advantage of this invention includes the removal of the necessity of an attenuation measurement. This is significant, as at these low microwave frequencies, the attenuation measurement has a very low correlation to the moisture content of the material. Given this poor correlation of attenuation to moisture at these low microwave frequencies, the prior art techniques discussed earlier will not provide a useful system for the determination of moisture. Even in situations where the attenuation could be utilized, by omitting this measurement and the associated circuitry, the system can be produced at a significant cost advantage. Other advantages are in the invention's ability to measure the propagation delay of the direct path signal as a function of the received frequency difference rather than as a phase delay measurement. This transformation of the propagation delay from a phase measurement to a frequency difference measurement removes the integer rollover experienced with a phase measurement. Thus, in the propagation delay measurement method utilizing a direct phase difference measurement method, the phase difference is limited to +/−180 degrees before the measurement repeats itself. This leads to a phase ambiguity in the processed signal. Conversely the frequency difference measurement of this invention does not suffer from this phase ambiguity issue and as such can provide a much larger measurement of propagation delay than the direct phase-delay method. This is highly advantageous in some measurement configurations where, due the large depth of the material under test, the expected electrical permittivities will cause a phase delay range that exceeds 360 degrees, leading to an ambiguous phase delay measurement due to the roll over of the phase measurement.

The specifications and tolerance of this type of system can be inferred from single frequency continuous wave (CW) measurements. In the CW system, it is noted that the phase as measured for a given test specimen, it also a function of the frequency. While Maxwell's equations predict the variation to be only a function of frequency and not the material, in practice due to the frequency dependence of the permittivity of material this is not the case. Thus, a very accurate, stable and repeatable method must be utilized to vary the reference frequency and therefore ensure that frequency drift of the oscillators will not compromise the measurements.

One preferred technique for varying the frequency is to provide a modulating frequency that is phase locked to a very stable oven-temperature controlled crystal oscillator. In this manner the carrier frequency can be modulated in a very precise and stable manner with variation of the carrier frequency determined by the frequency range of the modulating voltage controlled oscillator (VCO).

Figure 1B:
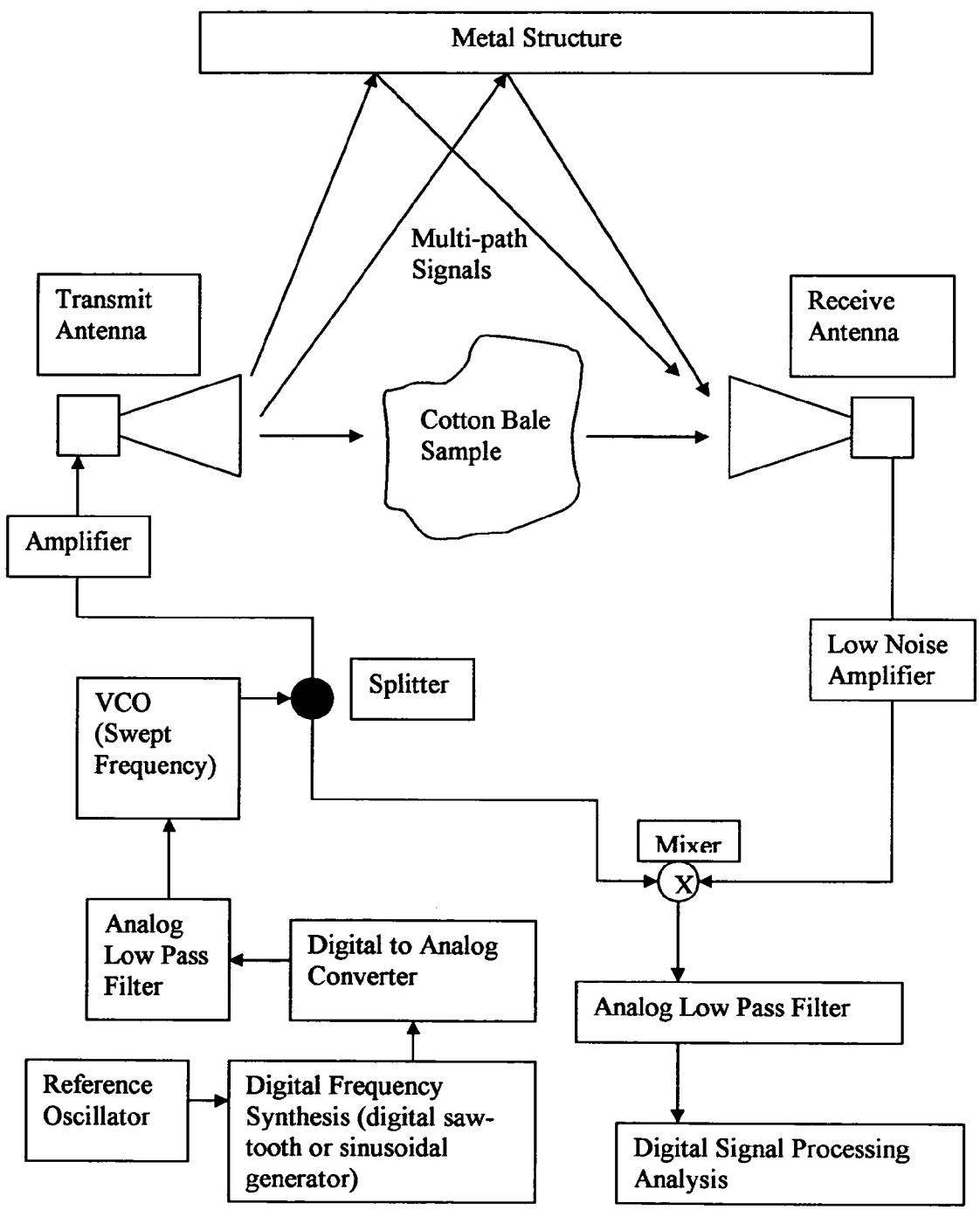
FIG. 1b is a schematic layout of the cotton bale moisture sensor with multipath interference detailing digital frequency synthesis and analog filtering of sinusoidal or sawtooth voltage control signal and subsequent digital signal processing of final signal.
Figure 1C:
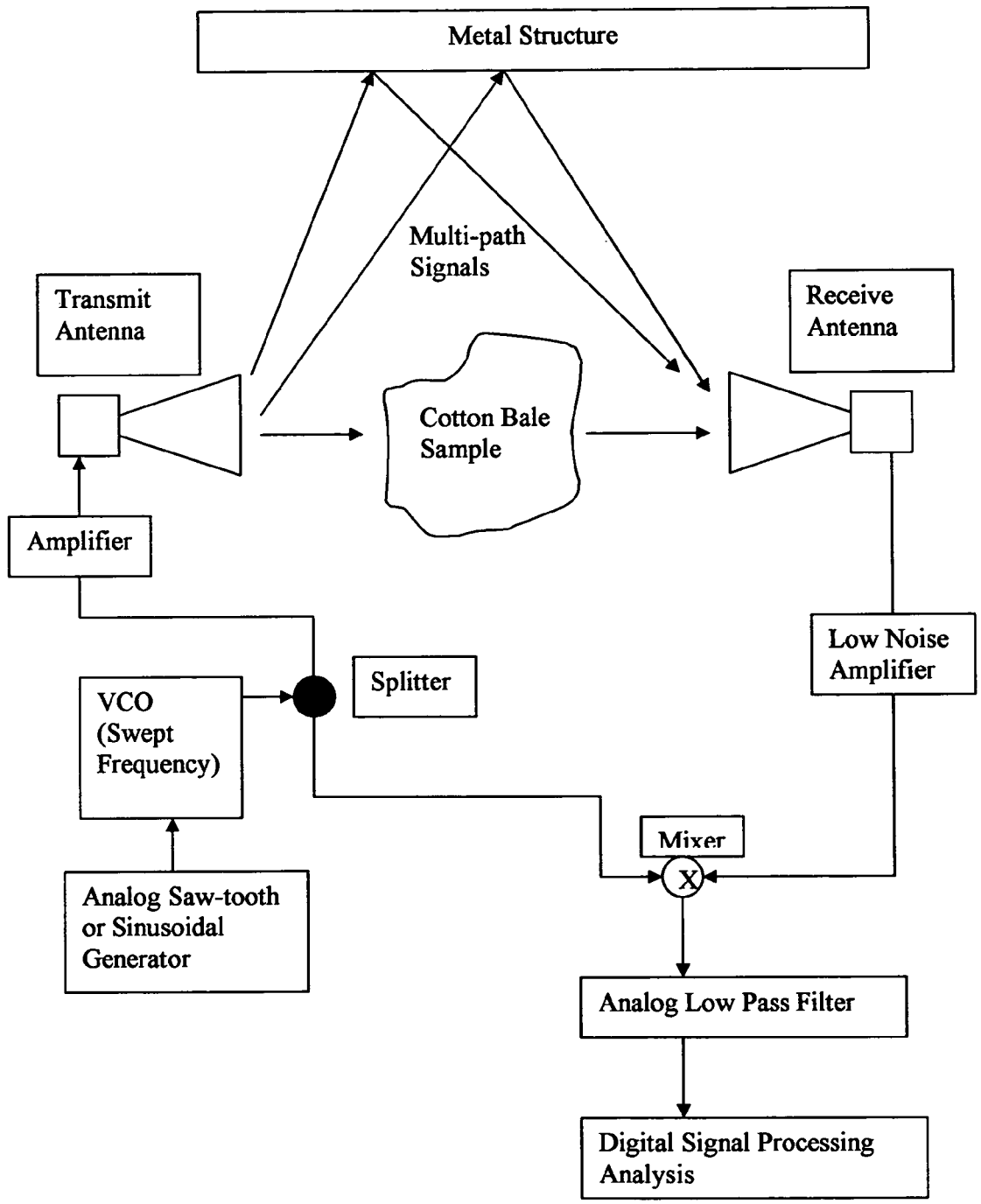
FIG. 1c is a schematic layout of the cotton bale moisture sensor with multipath interference detailing analog frequency synthesis of sinusoidal or saw-tooth voltage control signal and subsequent digital signal processing of final signal.
Figure 1D:
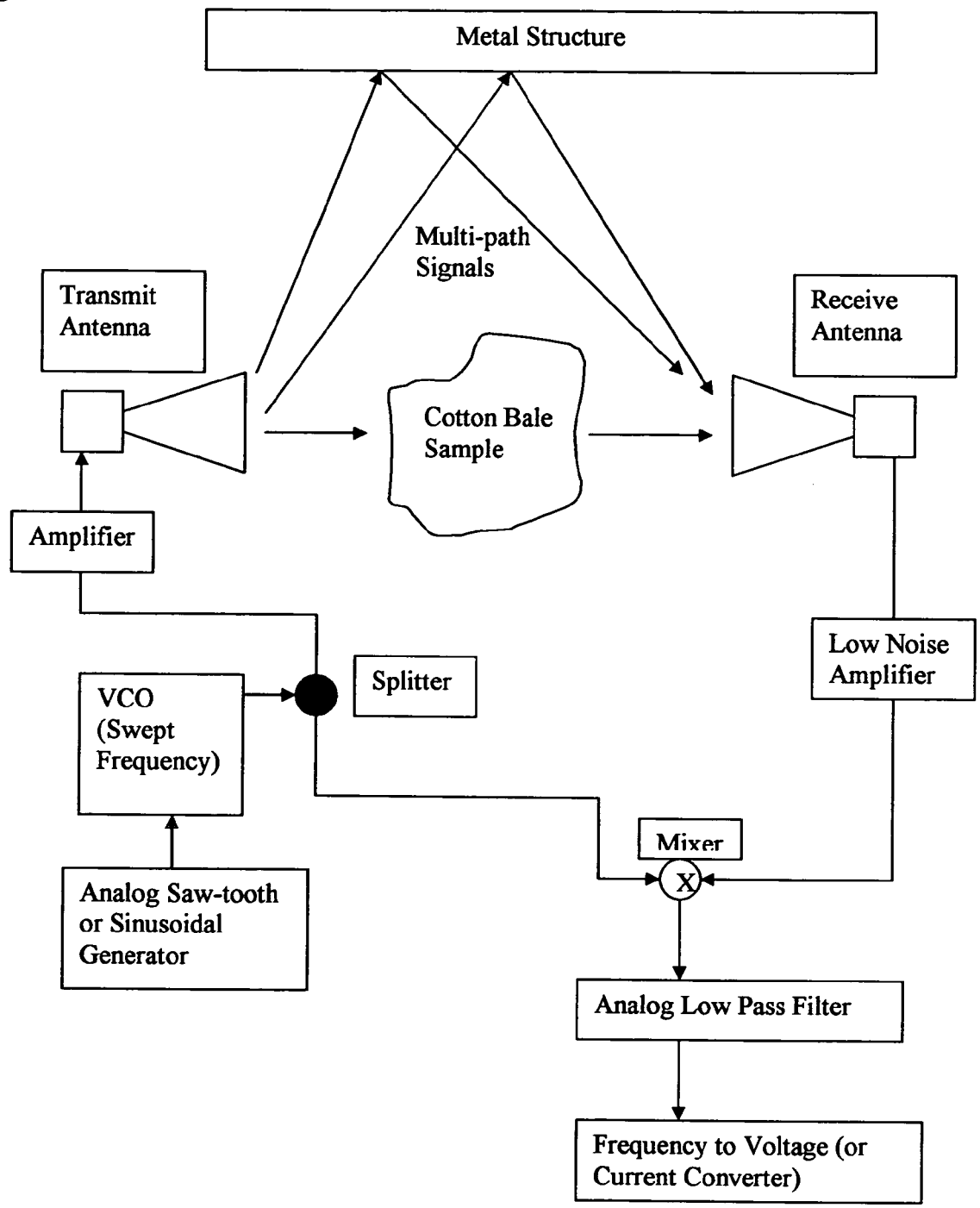
FIG. 1d is a schematic layout of the cotton bale moisture sensor with multipath interference detailing analog frequency synthesis of sinusoidal or saw-tooth voltage control signal and subsequent analog signal processing of final signal.

FIGS. 1a–d show an apparatus of a first embodiment for measuring cotton bales. The apparatus includes a method of producing a time varying control signal that is used as an input to a VCO with the primary purpose of all of these techniques is providing a frequency output from the VCO that is time-varying. In this invention this time varying signal can be of any repeatable form with examples such as a sinusoid or sawtooth or ramp wave form being suitable forms that can readily be adapted to this technique with the preferred waveform for this invention being the sawtooth. In FIG. 1a, two voltage controlled oscillators are used for this purpose. The lower frequency oscillator (10–100 MHz) is phase-locked to a temperature stabilized crystal oscillator through a phase-lock loop frequency synthesizer. This crystal oscillator will provide a stable frequency base for the modulating signal. The frequency synthesizer allows the stable modulating signal to be relocated to alternative frequencies during the measurement process. The output of this VCO (in either saw-tooth or continuous wave form) is then amplified to directly drive the high frequency VCO. FIGS. 1b–d show alternative methods of providing this time varying control signal. In FIG. 1b, it is generated by utilizing digital synthesis of the sinusoidal or ramp waveform in conjunction with an analog low pass filter to provide a good analog representation of this digital time-varying signal. In FIGS. 1c–1d, standard methods are used to provide an analog sinusoid or sawtooth ramp signal. It should be noted that it is possible to provide a strictly digital waveform without the use of an analog low pass filter if the time steps between subsequent steps in the digital waveform are less than 5 nano-seconds with the preferred step being less than 1 nano-second. At the output of the synthesis of the voltage control signal the optional addition of the amplifier/attenuator allows the system to adjust the peak to peak voltage range thereby providing control over the final peak to peak frequency deviation of the high frequency VCO. The modulating repetition frequency of the control voltage can be varied from 100 Hz to 100 MHz with the preferred range of modulation frequency being between 1 kHz and 100 kHz. This control voltage modulation is used to control the microwave VCO to output the transmitting signal that varies over a narrow frequency range about the target microwave frequency. One preferred example is to have this control voltage input to the VCO, control the VCO to output frequencies that range from 1.850 GHz to 1.875 GHz thereby providing a maximum frequency deviation of the transmitting signal of 25 MHz. It should be noted that while this maximum frequency deviation could be as large as 250 MHz it is desirable to utilize the smaller ranges for accuracy. Another preferred example is to have this control voltage input to the VCO, control the VCO to output frequencies that range from 2.50 GHz to 2.525 GHz. As detailed with these two examples, the target frequency has a degree of flexibility, however for use in cotton bale moisture measurement with metal bale ties, this target frequency range should be kept below around 3 GHz.

Figure 2:
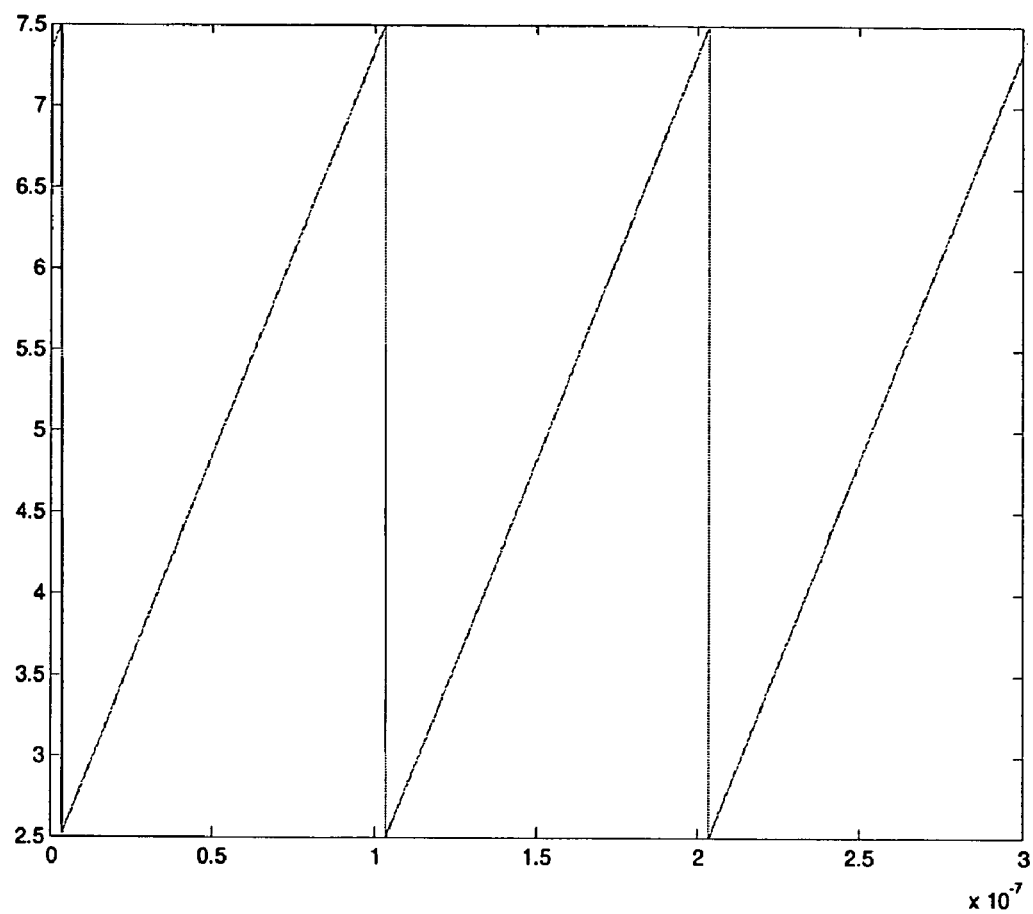
FIG. 2 is a frequency versus Time Plot of the Signal that is used to modulate the VCO in Example 1.
Figure 3:
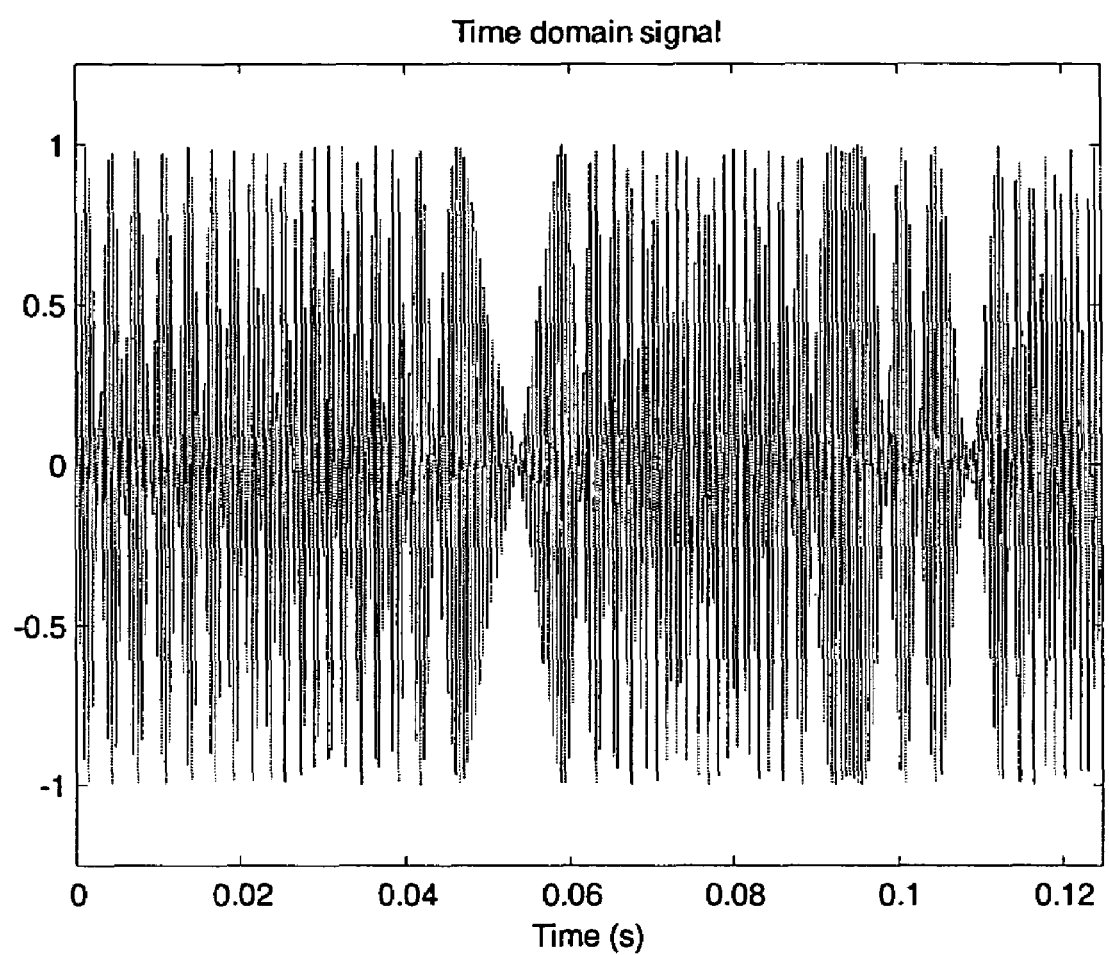
FIG. 3 is a time Domain Plot of the Transmitted Signal in Example 1.
Figure 4:
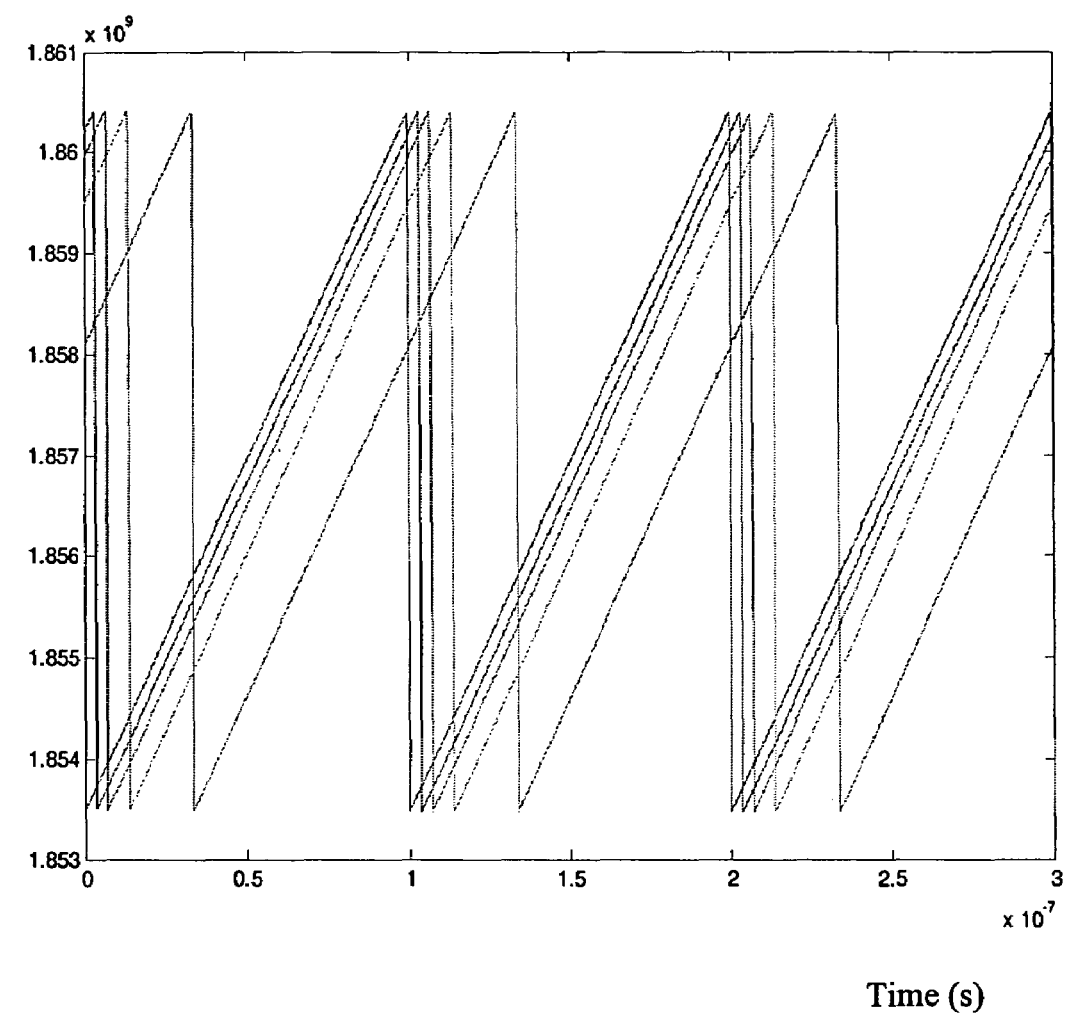
FIG. 4 is a Frequency versus Time Plot of the Received Signals. The first to arrive is the direct path signal and the others are the delayed multi-path signals in Example 1.

This embodiment provides a sinusoidal or saw-tooth swept signal that is used to transmit through the cotton bale. This signal is also used as the reference signal by splitting the signal and directing one as the reference and the other towards the transmitting antenna. The details of the system are shown in FIGS. 1a–d. These figures depict a method for providing a time varying control signal to provide frequency modulation of the transmitting VCO. As the preferred waveform for this invention is the sawtooth, the rest of the discussion will focus on this waveform, though it should be noted that equivalent results can be achieved with other waveforms. The frequency versus time response of this signal is detailed in FIG. 2. The signal in the time domain is shown in FIG. 3. During the transmission process, the signal spreads out into multiple directions leading to the signal taking different paths to the receiving antenna due to the reflection off of neighboring metal clad surfaces. As each of these paths are of differing lengths, the receiving antenna receives multiple copies of the original signal, all of which arrive at different times. This is shown in FIG. 4.

Figure 5:
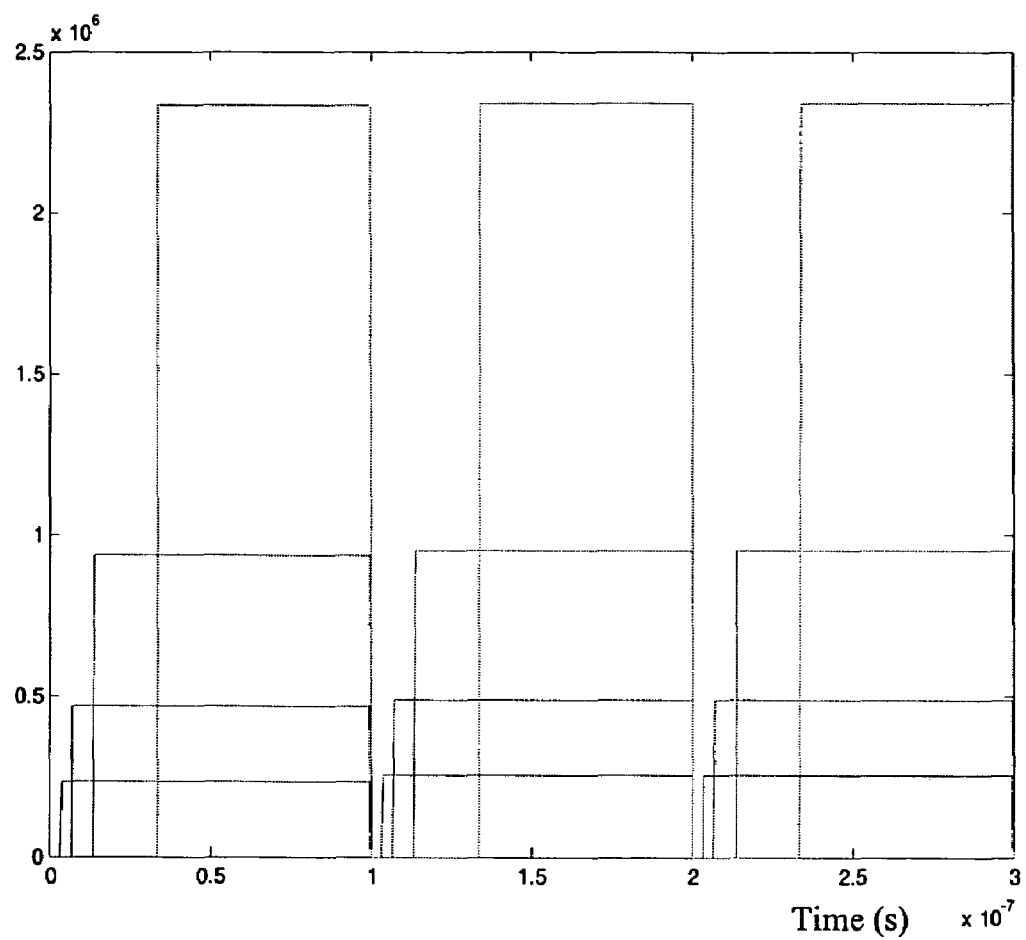
FIG. 5 is a theoretical plot of Frequency versus Time of the Received Signals after mixing to heterodyne signals to lower frequency in Example 1. The smallest frequency signal corresponds to the direct path signal and the others are the delayed multi-path signals.
Figure 6:
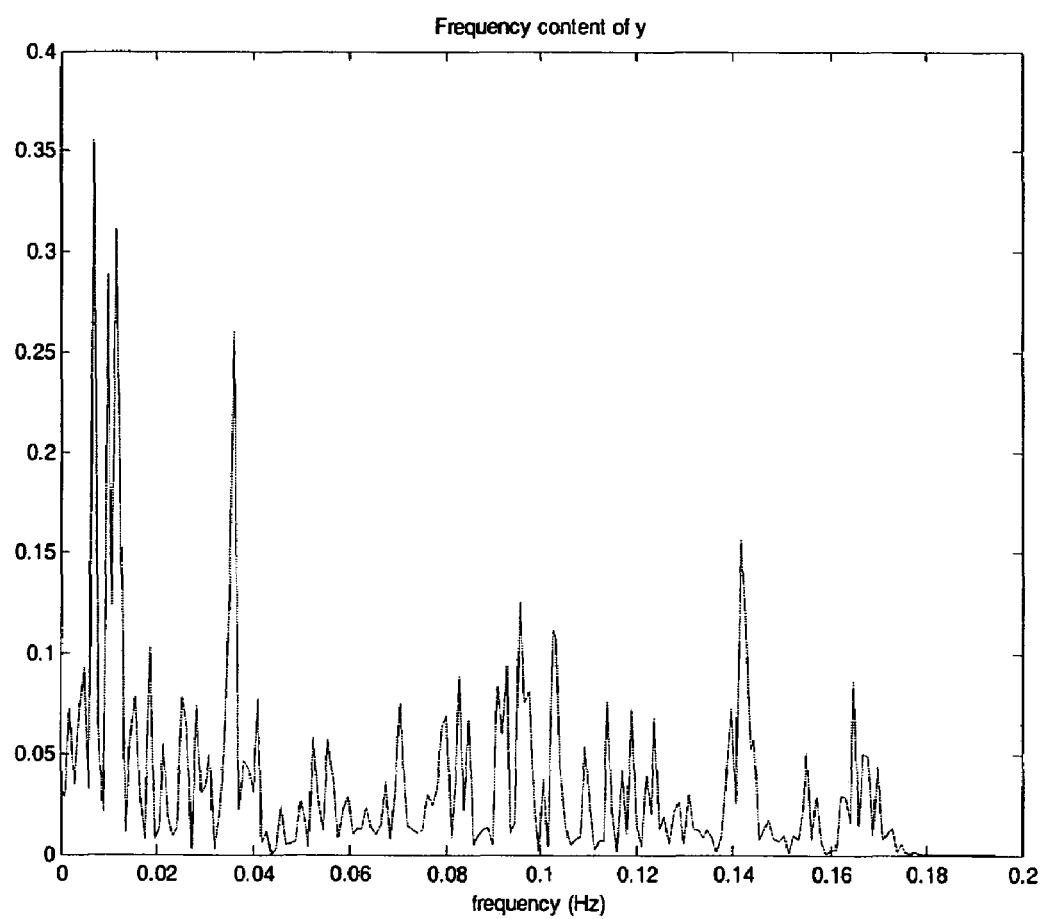
FIG. 6 is a power Spectral Density Frequency versus Time of the Received Signals after mixing (includes both the direct path plus all of the multi-path components) in Example 1.

Upon reception of the signal at the receiving antenna, the signal is passed through a low noise amplifier and then combined with the reference signal at a signal mixer. At this point the reference signal is at a higher frequency than the received signal. This is due to the longer propagation delay the signals undergo during transmission through free space as well as through the cotton bale than the reference which is transmitted internally over a short segment of coaxial cable. At the mixer, the sum and difference of these two frequencies are then produced due to the mixer's signal multiplication properties. Following the mixer, the sum and difference signal is passed through a low pass filter which removes the sum portion of the signal leaving only the difference signal. The theoretical difference frequency for the direct path signal as well as the further delayed multi-path signals is shown in FIG. 5. The direct path signal is the lowest frequency, in this figure, as it takes the shortest path to the receiving antenna. While the theoretical simplified equations provide insight, by transforming the time based signal into the frequency domain by means of a fast Fourier transform the true phenomena can be examined. This technique first subtracts the mean to remove the dc component and then utilizes a Hanning window to provide good spectral separation (Pozar, ibid) (Strum, R. D., and D. E. Kirk, 1988. First Principles of Discrete Systems and Digital Signal Processing. Addison-Wesley Publishing Co. Reading, Mass.) before performing the discrete Fourier Transform. The complex transform data is then multiplied by it's complex conjugate to form the power spectral density. FIG. 6 details the power spectral density of the received direct and multi-path signals in the frequency domain.

Figure 7:
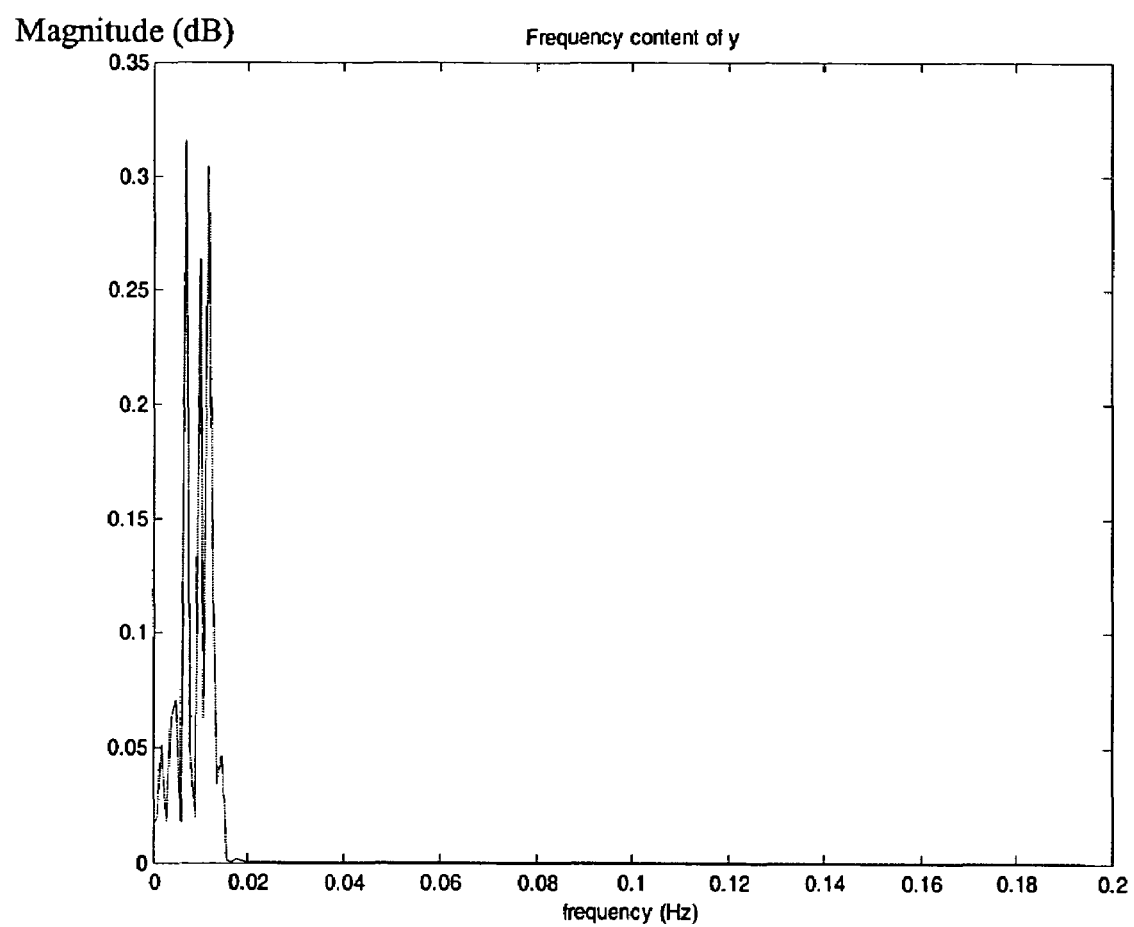
FIG. 7 is a power Spectral Density Frequency versus Time of the direct path signal in Example 1. The Fourier transform was performed after mixing the signal down to the base-band frequency.
Figure 8:
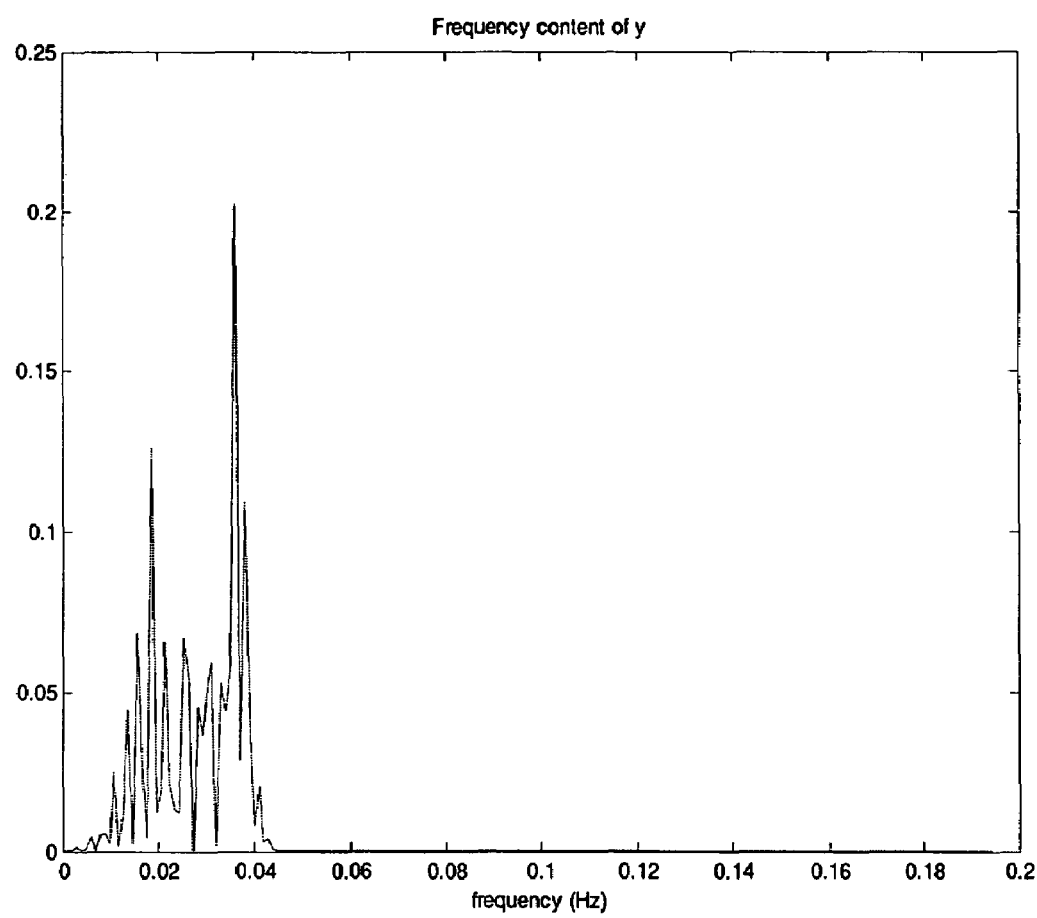
FIG. 8 is a power Spectral Density Frequency versus Time of the first multi-path signal to arrive at the receiving antenna in Example 1. The Fourier transform was performed after mixing the signal to the base-band frequency.
Figure 9:
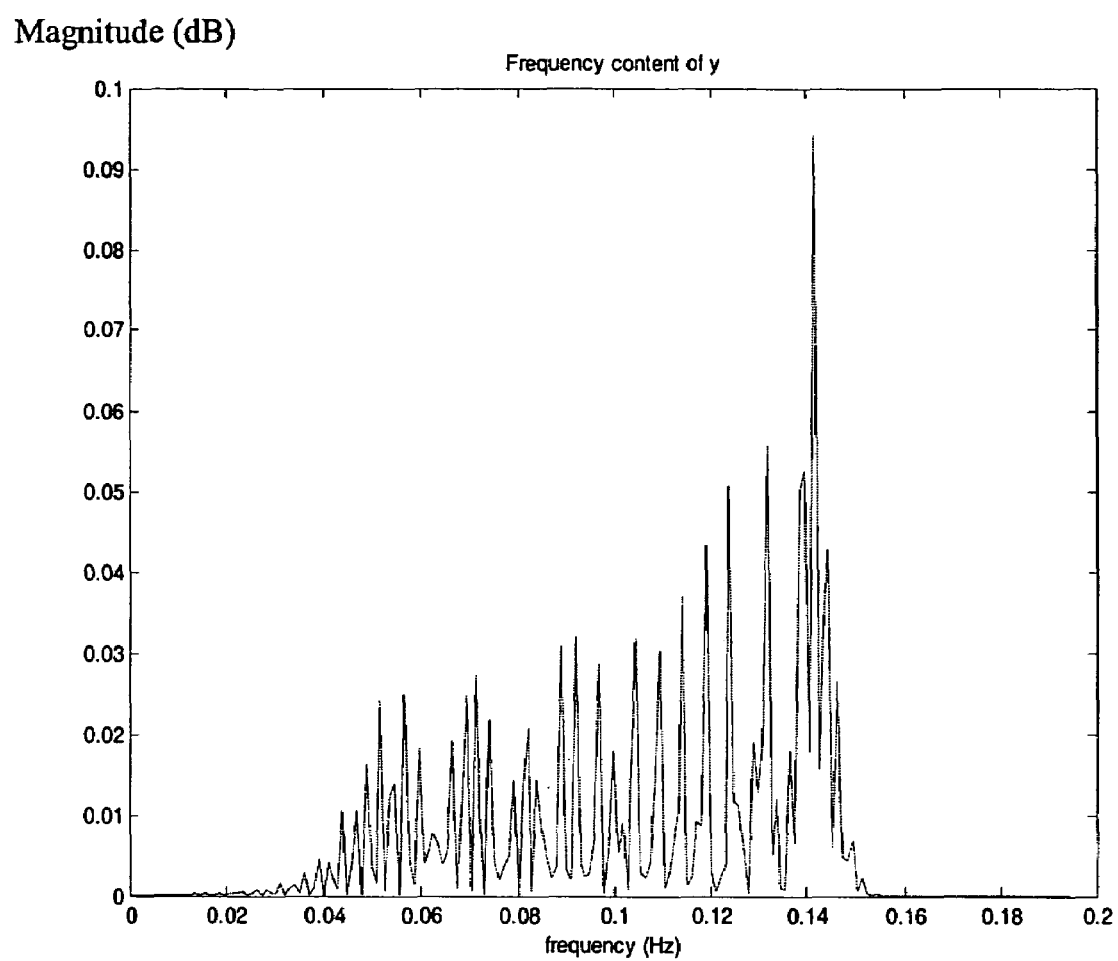
FIG. 9 is a power Spectral Density Frequency versus Time of the second multi-path signal to arrive at the receiving antenna in Example 1. The Fourier transform was performed after mixing the signal to the base-band frequency.
Figure 10:
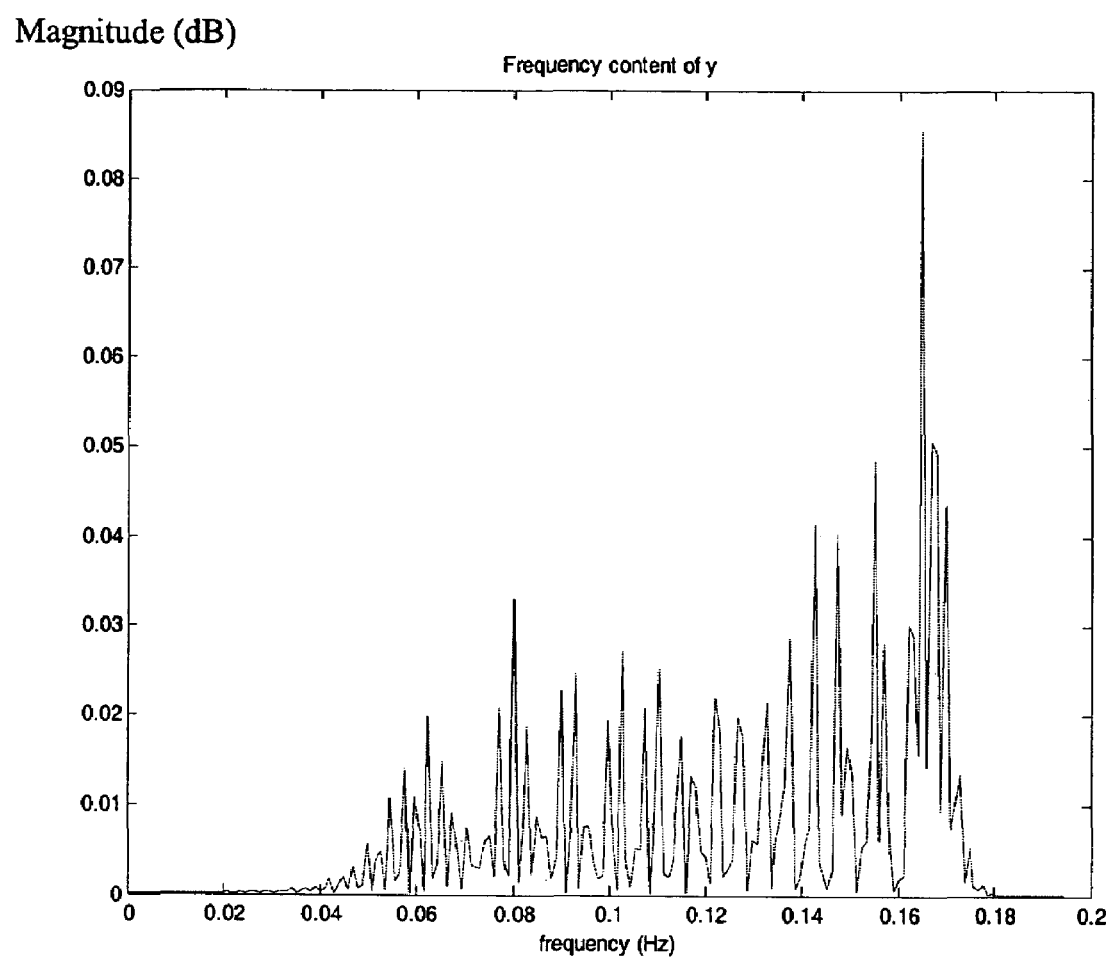
FIG. 10 is a power Spectral Density Frequency versus Time of the third multi-path signal to arrive at the receiving antenna in Example 1. The Fourier transform was performed after mixing the signal to the base-band frequency.
Figure 11:
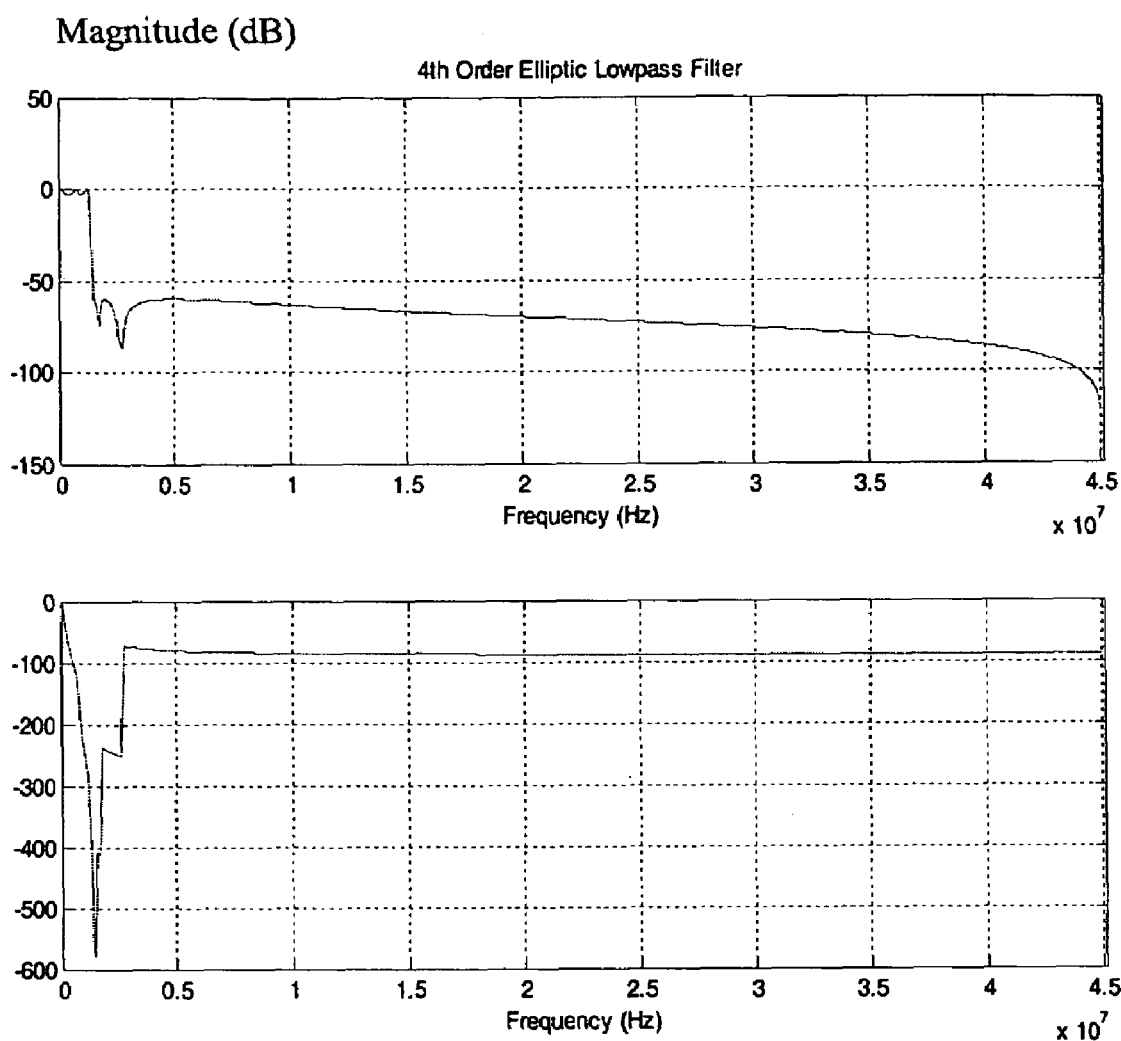
FIG. 11 is a digital Low Pass filter used to separate the direct path signal from the propagation delayed multi-path components in Example 1.
Figure 12:
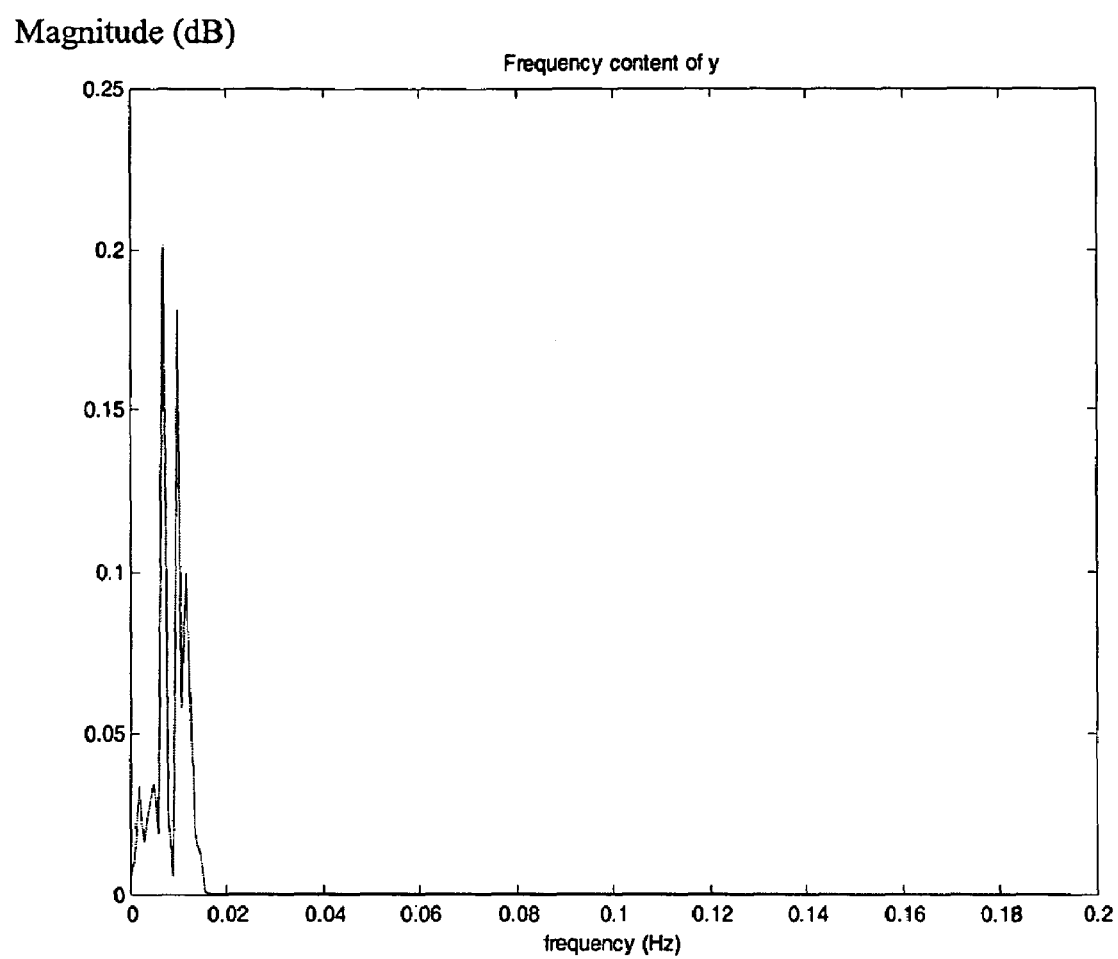
FIG. 12 is a power Spectral Density Frequency versus Time of all of the received signals (direct and all multi-path signals) that arrive at the receiving antenna in Example 1. The Fourier transform was performed after mixing the signal to the base-band frequency and after passing the digital low pass filter over the signal.

After reception, the signal is heterodyned down to the base-band frequency by mixing the received signals with the reference signal. Insight can be gained by examining. FIGS. 7–10 detail all of the received components separately; FIG. 7 shows the frequency domain of the direct path signal and FIGS. 8–10 detail each of the received multi-path components. Analysis of the figures demonstrate that the more delayed the signal the greater the spread in the frequency the signal becomes. This phenomenon is due to the increase in the modulation index resulting from the increased frequency difference between the reference and the multipath signal. This increase in the power sprading is advantageous as it's naturally providing additional filtering to the unwanted multi-path components. This analysis also demonstrates that the direct path component can be isolated from the multi-path components through a filtering process if a very sharp cut-off filter is applied to the data. Utilizing the frequencies detailed in FIGS. 7–10, an elliptic $8^{th}$ order low pass filter was designed (FIG. 11) for this purpose in the apparatus of the first embodiment.

After the mixing process, the signal is digitized and processed with a digital low-pass filter (or band-pass) that is designed to preserve only the frequencies where the direct path signal is located. This removes all of the other undesired components of the signal, such as the multi-path components, that lie outside this narrow frequency window. The remaining signal may then be used to calculate the moisture content of the material from a calibration equation prepared using controls of known moisture content.

A detailed description of a particularly preferred, second embodiment of the invention is provided in Example 2 below. In this embodiment, the maximum frequency deviation ($f_d$) of the signal transmitted through the test material (i.e., the range between the highest and lowest frequencies generated by the VCO) may vary with the desired moisture resolution. The maximum frequency deviation and the frequency repetition rate ($f_r$), which is the rate at which the saw tooth repeats itself, are selected to provide good frequency separation between the wet and dry material response, as the final measurement is in the form of a sinusoid whose frequency correlates to the moisture content of the material. These values may be determined by routine experimentation. In cotton, use of high maximum frequency deviations provide measurements increasingly correlated with density rather than moisture, and thus the maximum frequency deviation is preferably low. Without being limited thereto, the maximum frequency deviation should generally be less than approximately 250 MHz, although a deviation less than or equal to about 100 MHz is preferred and a deviation less than or equal to about 50 MHz is particularly preferred. The frequency repetition rate should preferably be at least about 1 kHz when utilizing a 20 MHz frequency deviation. Other modifications can be achieved by utilizing a slower voltage control repetition rate ($f_r$). However, at the lower repetition frequency the closest multi-path interferer will have a much smaller frequency separation between the multi-path signal and the desired straight path signal. As such it will be much harder to remove the multi-path signal from the composite signal through the filtering process.

The actual frequency of the signal transmitted through the material may vary and is not critical. However, because the dielectric constant of water increases with higher frequency, use of high frequencies above the 3.0 GHz range and up to 5.0 GHz may necessitate the use of smaller maximum frequency deviations ($f_d$) which in turn can limit the accuracy of the measured final frequency. Moreover, in cotton bales, at high frequencies the metal bale ties may cause interference. In general, for cotton bales suitable frequency ranges include but are not limited to between about 1.0 and 3.0 GHz, with frequencies between about 1.5 and 3.0 being preferred, and frequencies between about 2.5 and 2.6 being particularly preferred.

One preferred method of generating the signals to be transmitted through the material and to be used as the reference is to utilize a direct digital synthesizer to create the control voltage signal that is frequency locked to a temperature stabilized crystal oscillator reference. The output of the synthesizer is then filtered to remove or smooth the discrete steps created by the digital synthesis process. In an alternative preferred embodiment, also described in Example 2, rather than generating signals with continuously varying frequencies, the system may generate signals with discretely time varying frequencies. For example, discrete time varying signals may be produced using a digital method of generating the sinusoid or saw-tooth and then follow this digital to analog synthesis device with an analog low pass filter to smooth out and remove or almost remove the steps from the wave form. It is also envisioned that the discrete time varying signals may also be produced using a completely digital method of generating the signal at a rate sufficient to ensure the signals will be at different frequencies upon arrival at the mixer. Another alternative method of providing the control voltage signal is to utilize standard methods to produce an analog sawtooth waveform. A variety of digital or analog synthesizers and analog low pass filters are suitable for use herein.

The control voltage is applied to the microwave voltage controlled oscillator (VCO) to generate the microwave signal with the described controlled, continuously varying frequency. A variety of digital or analog means to generate this signal would be acceptable. The continuously varying microwave signal is then split into two signals (signal 1 and signal 2) utilizing a power splitter, whereupon signal 1 will be transmitted through the cotton bale and signal 2 will be used as the internal reference signal.

Following transmission through the material, the transmitted signal is received and then mixed with the reference signal using any conventional microwave mixer as described by Pozar (1998. Microwave Engineering. $2^{nd}$ Ed., New York: Wiley, the contents of which are incorporated by reference herein). This mixed signal is then passed through an analog anti-aliasing low pass filter. A variety of analog filters may be used, provided that the stop band of the filter is such that the frequency components that are located above two times the desired sampling frequency are rejected in order to avoid aliasing of these frequency components into the signal during the digitization stage that will be performed in a subsequent step (Porat, B. 1997. A course in digital signal processing. New York, John Wiley and Sons, Inc., the contents of which are incorporated by reference herein). This analog filtered mixed signal is then preferably applied to a second, digital band pass filter to remove substantially all of the multipath interfering signals which may be present. Although a band pass filter will provide the best performance and is therefore preferred, a low pass filter may be utilized. Moreover, rather than using an analog and digital filter, all filtering may be performed all in the analog domain, at the cost of loss of flexibility and stability of the filtering operation.

For digitally filtered signals, the output digital waveform is then analyzed digitally to determine it's frequency, and the frequency of this signal is the measurement of the propagation delay times the rate of change of the transmitted signal's frequency. Thus, this measurement provides a direct method to quantify the propagation delay of the transmitted signal. In the event that all of the filters are analog, either the analog band-pass signal could be digitized and similarly analyzed or a frequency to voltage converter can be utilized to obtain a voltage signal suitable for process control. One advantage to the use of digital filters is that these filters may be fine tuned to reject the maximum amount of multi-path interference as possible. Another advantage of generating the control signal and filtering in the digital domain is that it allows the system to repeat the entire measurement utilizing a different voltage control frequency, thereby giving the system the ability to reject multi-path signals that are at a distance such that they show up after the ramp signal has started to repeat the waveform thereby making this particular multi-path signal appear within the bandpass window and thereby causing interference with the desired straight-path signal. This is known as roll-over interference. When performing this technique multiple times with each time utilizing a different control voltage frequency repetition rate as described below, the answers from each test can be averaged to reduce the effect of these roll-over multi-path signals.

Once the final frequency of the filtered signal has been obtained this frequency can be utilized to calculate the propagation delay or time it takes for signal 1 to be transmitted through the material under test. This propagation delay is typically quantified by the phase velocity or the phase constant of material. Hence, once any or all of these parameters has been determined, they can be used to determine the permittivity of the material and/or moisture content of the material as described in detail in Example 2.

Calibration of the system propagation delays can be quantified by conducting an initial and/or measurement(s) without the material to be tested. After obtaining both the air propagation delay and the material plus air-instrument propagation delay the final measurement is then the difference between these two readings. This final measurement provides a true propagation delay of the material and therefore a measure of the material's permittivity as well as a measure of the moisture content of the material for a given material density and path length. In situations where the material and path length are well controlled no other information is required, such as is the case for moisture measurement of cotton bales. In other situations or to improve the accuracy both the density and the path length can be obtained through conventional means to improve the moisture measurement.

As noted above, the effects of roll-over interference may be minimized repeating the measurement in a series of tests. In each test a different control voltage repetition rate ($f_r$) is utilized. The results of each of these tests may then be averaged to obtain the final measurement.

In addition to the above mentioned signal generator, transmitter, receiver, mixer, filters, and frequency detector, the apparatus may also include an optional microprocessor based computer control unit (CPU) effective for receiving and measuring the frequency (of the filtered-mixed signal) and calculating the moisture content therefrom.

Conventional interface hardware are also provided allowing communication between the microprocessor and the frequency detector. The microprocessor includes hardware and software effective for determining the moisture content. The microprocessor is preferably constructed with an output for displaying or presenting results, and a communications link or input allowing it to be interrogated and/or reprogrammed by the user.

The process and apparatus of the invention may be used to determine the moisture content of a wide variety of materials. Without being limited thereto, the invention is particularly suited to the measurement of moisture of materials disposed within buildings or environments subjected to multipath interference. Non-limiting examples of such materials include cotton, grass, hay, grain, tobacco, timber, lumber, and paper pulp, and particularly cotton bales.

The following examples are intended only to further illustrate the invention and are not intended to limit the scope of the invention which is defined by the claims.

EXAMPLE 1

The apparatus of the above-described first embodiment and shown in FIG. 1 was used to measure the moisture of baled cotton. This technique was analyzed with the multi-path interference modeled by a set of three delayed signals that was added at the receiving antenna to the received signal. The delayed multi-path signals consisted of a 3, 5, 7 and 20 m signal delay. This delay is due to the signal propagating out into multiple directions with each of these separate signal vectors following a longer path to the receiving antenna as discussed earlier. As is standard in the telecommunications industry, the signal strength of the interference can be reduced in signal strength to a fraction of the transmitted signal (Stremler, ibid). Typical values used in this type of modeling suggest levels of less than 10%, however in this case it was felt that a 100% signal strength level would be a better indication of success as the distances involved are very small and there is no real attenuation expected from distance effects. As such all of the attenuation effects will be due solely to the front to back ratio of the horn antennas as the multi-path signals are created from a fraction of the total transmitter power. A typical microwave horn will exhibit a front to back radiation ratio of 10–15 dB, which corresponds to a signal strength of a less than 20% of the direct path signal strength (Cheng, ibid) (Balanis, ibid). As such, this model will be conservative and should provide a good indication of the worst case potential of the system in practice.

The frequency differences of the delayed signals were calculated based upon the expected extra path length of the multi-path components. The direct path signal delay was calculated based upon the expected delay due to free space separation as well as the expected delay due to the cotton bale at two levels of moisture 4.5% and 8.5%, that represent the extremes for the expected range of operation for the unit. These expected phase delays were obtained from laboratory experiments on commercially obtained cotton bales of varying moisture contents and densities across the range of frequencies from 1.5 GHz to 2.5 GHz.

Figure 13:
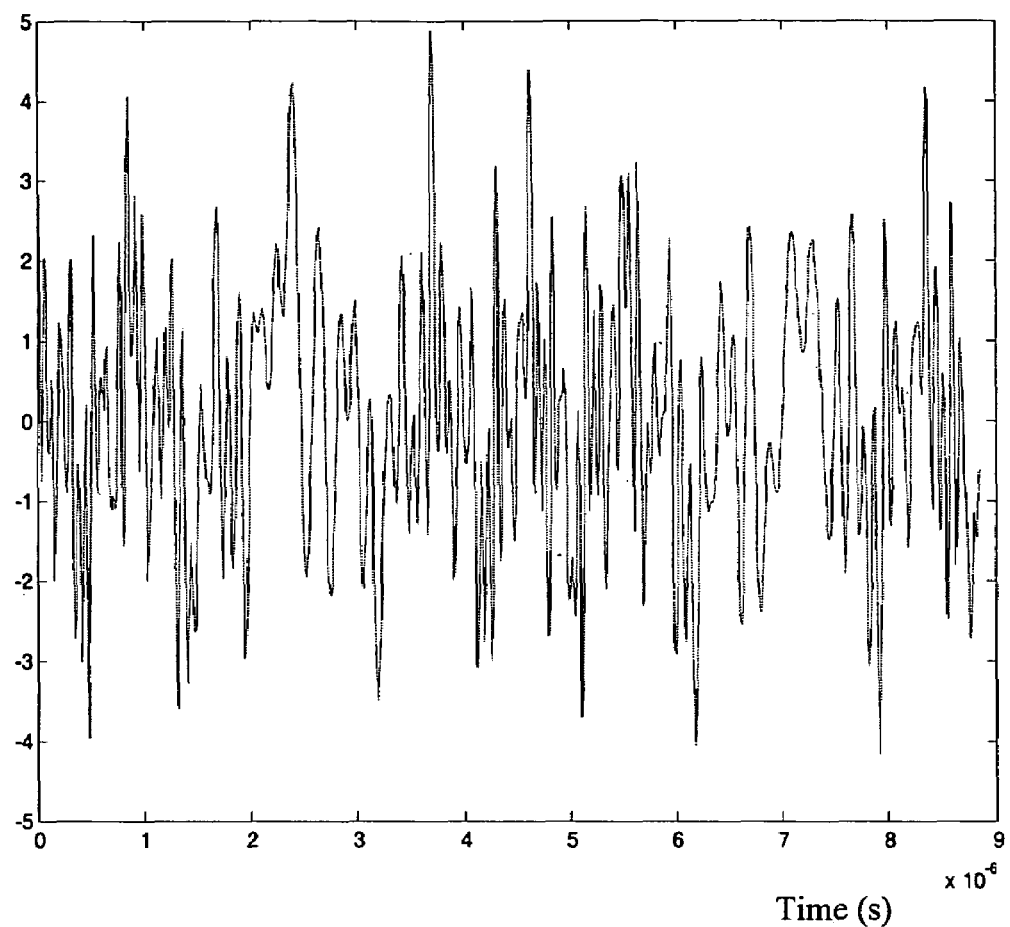
FIG. 13 is a time domain plot of all of the received signals (direct and all multi-path signals) that arrive at the receiving antenna (after mixing the signal to the base-band frequency) in Example 1.
Figure 14:
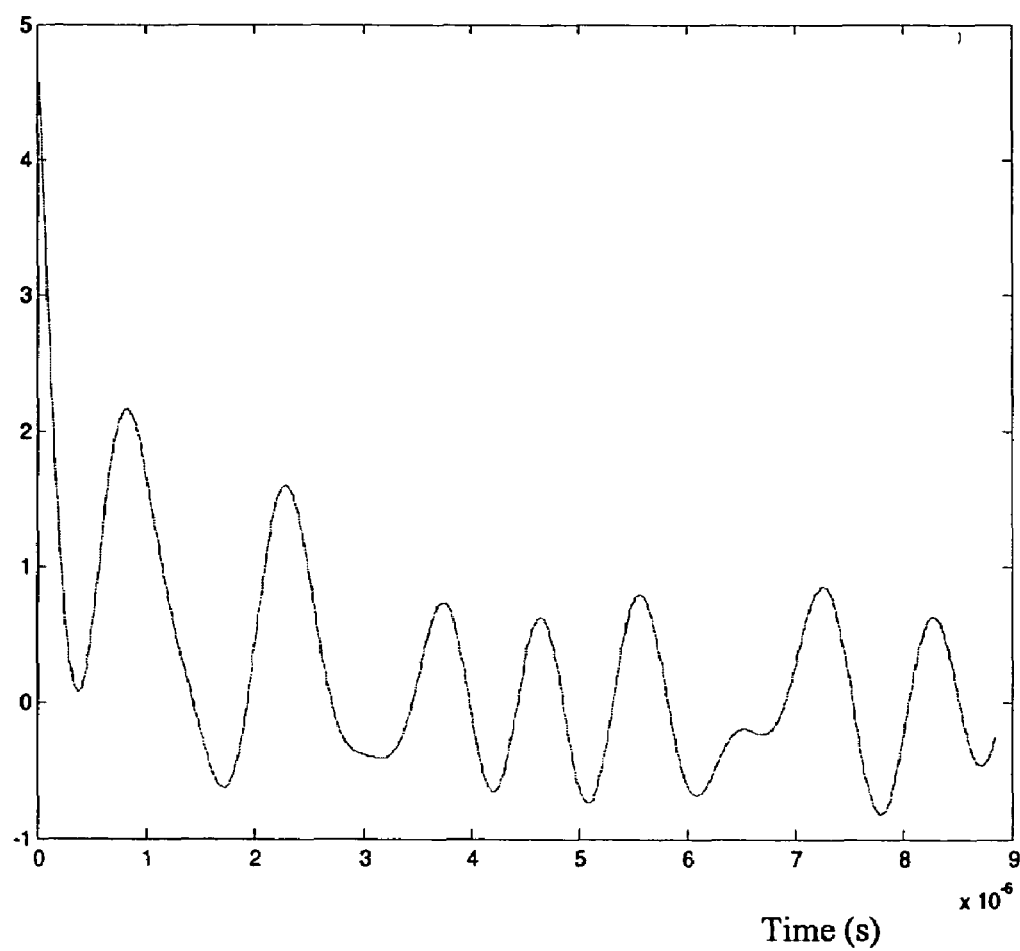
FIG. 14 is a time domain plot of all of the received signals (direct and all multi-path signals) that arrive at the receiving antenna (after mixing the signal to the base-band frequency and after digital low pass filtering) in Example 1.

Once the target window was identified, the response of a filtered window centered about that frequency was examined. The performance of this system could be inferred by comparing both dry cotton to wet cotton with and without the presence of the multi-path interferers. Utilizing the previously described techniques, the system with the addition of the three multi-path interferers after mixing produced a time domain signal as shown in FIG. 13. After applying, the previously designed digital low pass filter, to this signal the direct path signal was recovered and is shown in FIG. 14. The system then measured the average frequency of this recovered signal to provide a measure of the cotton moisture.

This invention provides a system that automatically repeats the waveform, thereby increasing the signal strength through repetition. As this feature causes the system to start over at some future delta-t, when it does so it is possible that a long multi-path signal will be just arriving at this time as well. This leads to an ambiguity between the direct path and this long multi-path signal. This exact length can be calculated by the frequency of the multi-path signal as t=1/f which leads directly to the path length of ambiguity of distance=c/f. For this system, this distance occurs at 28 m. To remove this effect the signal measurement can be repeated at a different repetition frequency where that specific ambiguity multi-path signal will appear in a different portion of the frequency domain thereby removing its effect from the measurement. In this way, the system can also remove this multi-path signal from the direct path signal. As it is possible that a new multipath signal will now appear at this ambiguity distance, this process should be repeated numerous times to obtain multiple readings by which to extract the true propagation delay through an averaging or filtering process on these replicated readings.

EXAMPLE 2

A preferred apparatus was constructed for measuring the moisture of cotton bales. This system assumes a cotton bale density such that an industry standard Universal Density bale (UD bale weighs approximately 500 lbs, and a path length of the material of 21 inches (the short dimension of the UD bale through which the signals will be transmitted.

The following steps were performed two times; once with no material between the antennas (air-instrument propagation delay measurement) and again with the cotton bale or material under test located between the two antennas (material plus air-instrument measured propagation delay). After obtaining both the air propagation delay and the material plus air-instrument propagation delay the final measurement is the difference between these two readings after correction for the rate of frequency deviation. It is this final measurement that provides a measure of the permittivity of the material as well as the moisture content of the material for a given material density and path length.

Step 1: Generate a control voltage in the form of a Saw Tooth or Sinusoidal waveform whose voltage range is such that the preferred maximum frequency deviation of the voltage controlled oscillator (VCO) is less than 20 MHz in order to achieve an accurate measure of moisture. The frequency repetition rate should be at least 1 kHz when utilizing a 20 MHz frequency deviation. In the generation of this control voltage signal it is imperative that either a continuously varying analog signal is utilized or in the case of digital synthesis techniques that the rate of change between the discrete voltage steps are rapid enough to ensure that the received signal 1 is at a different frequency than the internal reference signal 2 when both arrive at the mixer of steps 5 and 8. It should be noted that in the discrete generation version of producing the control voltage, the digital to analog conversion should be utilized in conjunction with an analog low-pass filter in order to obtain a smooth transition between the discrete steps. This will reduce the required sampling rate that would otherwise be necessary to achieve the requirement of signal 1 and signal 2 arriving at the mixer as two separate frequencies. In the omission of this analog filter, the system will have the requirement that the step change rate between discrete voltage levels has to be greater than 300 MHz. As digital synthesis technique results in a very stable and repeatable signal that is inherently temperature independent, this control voltage signal is preferably generated utilizing digital synthesis technology in conjunction with an analog low pass filter. The preferred method of producing this signal is to over-sample the desired frequency repetition rate by at least 8 times and utilize a low order analog low pass filter whose corner frequency is set to 2 times (Valkenburg, M. E., 1982. Analog Filter Design. Holt, Rinehart and Winston, New York). One suitable device to generate this signal is an Analog Devices (Norwood, Mass.) AD9832 direct digital synthesizer that is frequency locked to a temperature stabilized crystal oscillator reference in conjunction with standard methods for analog low pass filtering. Alternatively this signal could be an analog continuously varying signal created utilizing standard methods for generating sinusoids or saw-tooth waves.

Step 2: Apply the control voltage of step 1 to the microwave voltage controlled oscillator (VCO) having a specification rating suitable to generate a range of frequencies ranging 1.73 GHz to 1.75 GHz for the applied control voltage input as previously discussed in step 1, hereafter known as signal 0, when the voltage control signal of step 1 is input to this VCO. One such suitable VCO is the 790-1750t VCO manufactured by VariL Corp (Broomfield, Colo. 80021).

Step 3: Provide either a loss-less or resistive T junction power divider (Pozar, ibid) to split the signal into two signals; signal 1 and signal 2. Signal 1 will be used to transmit the signal through the cotton bale and signal 2 will be used as the internal reference signal.

Step 4: Convey signal 1 to an amplifier by means of a coaxial cable.

Step 5: Convey signal 2 to a microwave double-balanced mixer (Pozar, ibid).

Step 6: Convey amplified signal 1 to a microwave horn or other type of directional antenna with a preferred signal focusing or gain of at least 10–20 dB (Balanis, C. A. 1982. Antenna Theory, analysis and design. New York, Harper & Row). This horn or antenna is to be located on one side of the cotton bale or other material under test such that the majority of the signal is transmitted through the cotton bale or other material under test. It should be noted that this technique will work with any type of antenna and that the use of directional type of antenna is specified in order to achieve the best possible performance.

Step 7: Place a receiving antenna of similar design to the transmitting antenna utilized in step 6, on the opposite side of the cotton bale or material under test. This antenna should be oriented such that the best reception of the transmitted signal will be received (Balanis, ibid).

Step 8: Convey received signal 1 by means of a coaxial cable to the double-balanced mixer of step 5.

Step 9: Mix the signal 1 with signal 2 in the double-balanced mixer of step 5 and step 8 to form signal 3.

Step 10: Convey signal 3 by means of coaxial cable to an analog anti-aliasing low pass filter to form a filtered version of signal 3 hereafter labeled signal 4. In the preferred embodiment the filter will be constructed to have the following specifications; the corner frequency is less than 300 kHz, the passband ripple is less than 3 dB, and the stop band attenuation is greater than −40 dB in relation to the passband signal (Valkenburg, M. E., 1982. Analog Filter Design. Holt, Rinehart and Winston, New York).

Step 11: Convey signal 4 to an analog to digital converter. This a2d must sample signal 4 at a frequency that is greater than two times the stop band frequency of the analog low pass filter that was utilized in step 10 (Porat, ibid). For this example the preferred sampling frequency is greater than 1 MHz. This analog to digital captured signal in digital form (data) will hereafter be referred to as signal 5.

Step 12: Apply a digital band pass filter to the data of signal 5. This digital filtered is designed with the first corner frequency occurring at the same frequency that the air-instrument signal occurs. The second corner frequency will be placed at the frequency of where the material air-instrument occurs at the highest moisture content of interest. For this example; this digital band pass signal is constructed with the following specifications; the first corner frequency will be 0.01 pi, the second corner frequency will be 0.02 pi, the stop band will be attenuated to below −40 dB in relation to the passband, and the preferred roll-off of the corner frequencies will be greater than minus 80 dB/decade (Porat, ibid).

Step 13: The output digital waveform from step 12 is then analyzed digitally to determine it's frequency. The frequency of this signal is the measurement of the delay. Thus, in the all-analog variant of step 12, either the analog band-pass signal of step 12 could be digitized and similarly analyzed as outlined earlier in this step or a frequency to voltage converter can be utilized to obtain a voltage signal suitable for process control.

Step 14: Once the final frequency of the filtered signal 5 has been obtained this frequency can be utilized to calculate the propagation delay or time it takes for signal 1 to be transmitted through the material under test. This propagation delay is typically quantified by the phase velocity or the phase constant of material. Hence, once any or all of these parameters has been determined, it can be used to determine the permittivity of the material from the following relations:

$$v_p = c/(u_r * e_r) \tag{7}$$

Where $v_p$=phase velocity [propagation velocity of the wave through the material] (m/s)

c:=velocity of light (m/s)

$e_r$:=permittivity of material under test (F/m)

$u_r$:=permeability of material under test (H/m)

Noting that the permeability of cotton and other biological products are essentially equivalent to that of air equation 1 can be simplified to equation 7b.

$$v_p = c/(e_r)^{1/2} \tag{7b}$$

$$t = L/v_p \tag{8}$$

$$df/dt = f_d * f_r \tag{9}$$

Where t:=transmit time for the wave (signal 1) to propagate through the material (s)

L:=signal propagation path length {thickness of material under test} (m)

df/dt:=frequency rate of change of the transmitted signal 1 (hz/s)

$f_d$:=maximum frequency deviation of signal 1 (20 MHz as discussed in step 1)

$f_r$:=repetition frequency of the output signal 1 (1 kHz as discussed in step 1)

$d_f$:=difference frequency between the internal reference signal and the received transmitted signal 1 as determined in step 13 (Hz).

To quantify the material under test independently of the system, it is necessary to take an air reference to provide a zero reference point and calibrate the system.

$$d_{f\_air} = t df/dt \tag{10}$$

$$d_{f\_mat} = t df/dt \tag{11}$$

$d_{f\_air}$:=difference frequency of the air reference $d_{f\_mat}$:=difference frequency as measured with the material under test.

In a preferred embodiment, the measurement of the material is independent of geometry, and therefore the path length of the propagation needs to be accounted for. The material is therefore characterized in terms of permittivity rather than a direct moisture calibration (though this is also easily done). After obtaining the permittivity of the material, the measured permittivity is related to the moisture content of the material (assuming either a knowledge of the material's density or obtaining the density by conventional means). Utilizing these basic relations from equations 7–11, we arrive at the function that predicts the permittivity of material $$e_r = [c(d_{f\_mat} - d_{f\_air})/(L(f_d * f_r))]^2 \tag{12}$$

Once the permittivity of the material under test is known, a function that relates the permittivity to the density and moisture of the material can be formulated from experimental data for the desired moisture and density ranges at the frequencies of interest. One such equation that can be utilized for this purpose for cotton is detailed in equation 13:

$$\% M.C. = [(5.397 \, (e_r)^{1/2}/\rho) - (5.193/\rho)] + 0.8844 \tag{13}$$

where

ρ:=density of the material (gm/cc)

It is understood that the foregoing detailed description is given merely by way of illustration and that modifications and variations may be made therein without departing from the spirit and scope of the invention.

I claim:

1. A process for determining the moisture content of a material comprising:

producing a primary microwave signal with a varying frequency, said signal being a continuously varying signal or a discrete time varying signal, splitting said primary signal to provide first and second microwave signals, said first signal to be transmitted through said material and said second signal comprising an internal reference signal, transmitting said first signal through at least a portion of said material, receiving at a receiver a third signal which comprises potential multi-path interference signals and said first signal which has passed through said material, mixing said third signal together with said second signal, generating a mixed signal, filtering said mixed signal to remove substantially all of said multi-path interference signals, generating a filtered-mixed signal measuring the frequency of said filtered-mixed signal to determine the propagation delay of said first signal after it has passed through said material, and calculating the moisture content of said material from said propagation delay of said first signal after it has passed through said material, wherein the frequency of said primary signal varies sufficiently rapidly that the frequency of said third signal and said second signal will be different when they are received at said receiver.

2. The process of claim 1 wherein said material is selected from the group consisting cotton, hay, grain, tobacco, timber, lumber, and pulp.

3. The process of claim 1 wherein said material comprises a cotton bale.

4. The process of claim 1 further comprising determining the density of said material, and wherein said moisture content is calculated from a calibration equation which utilizes said propagation delay and said density.

5. The process of claim 4 further comprising determining the transmission path-length of said first signal through said material, and wherein said moisture content is calculated from a calibration equation which utilizes said transmission path-length, said propagation delay, and said density.

6. The process of claim 1 wherein said primary microwave signal comprises a discrete time varying signal.

7. The process of claim 1 wherein said primary microwave signal comprises a continuously varying signal.

8. The process of claim 7 wherein said primary microwave signal whose frequency is continuously varying is produced by a microwave voltage controlled oscillator with a continuously varying voltage source.

9. The process of claim 8 wherein the frequency of said primary microwave signal produced by said voltage controlled oscillator varies over a range of less than about 250 MHz.

10. The process of claim 9 wherein the frequency of said primary microwave signal produced by said voltage controlled oscillator varies over a range of less than or equal to about 100 MHz.

11. The process of claim 9 wherein the frequency of said primary microwave signal produced by said voltage controlled oscillator varies over a range of less than or equal to about 50 MHz.

12. The process of claim 1 wherein said filtering of said mixed signal to remove substantially all of said multi-path interference signals comprises:

sampling said mixed signal with an analog to digital converter to form a discrete sampled mixed signal filtering said discrete sampled mixed signal with a digital filter to remove substantially all of said multi-path interference signals, thereby generating said filtered-mixed signal.

13. The process of claim 1 wherein the determination of said propagation delay comprises determining the phase-constant or phase velocity of said material.

14. The process of claim 1 further comprising determining the propagation delay in the absence of said material comprising:

transmitting said first signal through air in the absence of said material, receiving a third calibration signal which comprises said first signal which has passed through said air and potential multi-path interference signals, mixing said third calibration signal together with said second signal, generating a mixed calibration signal, filtering said mixed calibration signal to remove substantially all of said multi-path interference signals, generating a filtered-mixed calibration signal measuring the frequency of said filtered-mixed calibration signal to determine the propagation delay of said first signal after it has passed through said air, and calculating the moisture content of said material from said propagation delay of said first signal after it has passed through said material and said propagation delay of said first signal after it has passed through said air.

15. The process of claim 1 wherein said frequency of said first signal varies at a first controlled repetition rate.

16. The process of claim 15 wherein said first controlled repetition rate is greater than or equal to about 1 KHz.

17. The process of claim 15 further comprising repeating all of said producing, splitting, transmitting, receiving, mixing, filtering, measuring, and calculating steps wherein said frequency of said first signal varies at a second controlled repetition rate which is different from said first controlled repetition rate, and determining a mean moisture content from the moisture content calculated at each of said first and second controlled repetition rates.

18. The process of claim 17 further comprising repeating all of said producing, splitting, transmitting, receiving, mixing, filtering, measuring, and calculating steps wherein said frequency of said first signal varies at numerous controlled repetition rates which are different from said first controlled repetition rate, and determining a mean moisture content from the moisture content calculated at each of said first and other controlled repetition rates.

19. The process of claim 1 wherein the frequency of said primary microwave signal varies over a range of less than about 250 MHz.

20. The process of claim 19 wherein the frequency of said primary microwave signal varies over a range of less than or equal to about 100 MHz.

21. The process of claim 20 wherein said material comprises a cotton bale.

22. The process of claim 19 wherein the frequency of said primary microwave signal varies over a range of less than or equal to about 50 MHz.

23. The process of claim 22 wherein said material comprises a cotton bale.

24. An apparatus for automatically determining the moisture content of a material comprising:

a microwave signal generator effective for producing a microwave signal with either a continuously varying frequency or a discrete time varying frequency, a microwave signal transmitter effective to transmit said microwave signal through the material, a microwave signal receiver effective to receive said microwave signal after it has passed through said material, a microwave signal mixer effective for mixing said microwave signal received by said receiver and a reference signal to generate a mixed signal, a microwave signal filter effective to remove substantially all multipath interference signals to generate a filtered-mixed signal, and a frequency detector effective to determine the frequency of said filtered-mixed signal, wherein the frequency of said primary signal varies sufficiently rapidly that the frequency of said third signal and said second signal will be different when they are received at said receiver.

25. The apparatus of claim 24 further comprising a microprocessor coupled to said frequency detector and effective for calculating the moisture content from the frequency of said filtered-mixed signal.

* * * * *